(12) United States Patent
Lechner et al.

(10) Patent No.: US 12,233,147 B2
(45) Date of Patent: Feb. 25, 2025

(54) METHOD FOR TREATING KERATIN MATERIAL

(71) Applicant: Henkel AG & Co. KGaA, Duesseldorf (DE)

(72) Inventors: Torsten Lechner, Langenfeld (DE); Gabriele Weser, Neuss (DE); Claudia Kolonko, Remscheid (DE); Caroline Kriener, Duesseldorf (DE); Ulrike Schumacher, Duesseldorf (DE); Marc Nowottny, Monchengladbach (DE); Juergen Schoepgens, Schwalmtal (DE); Phillip Jaiser, Langenfeld (DE); Carsten Mathiaszyk, Essen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 666 days.

(21) Appl. No.: 17/601,401

(22) PCT Filed: Feb. 17, 2020

(86) PCT No.: PCT/EP2020/054100
§ 371 (c)(1),
(2) Date: Oct. 4, 2021

(87) PCT Pub. No.: WO2020/200574
PCT Pub. Date: Oct. 8, 2020

(65) Prior Publication Data
US 2022/0211601 A1 Jul. 7, 2022

(30) Foreign Application Priority Data
Apr. 4, 2019 (DE) .......................... 102019204807.2

(51) Int. Cl.
| | |
|---|---|
| *A61K 8/58* | (2006.01) |
| *A61K 8/31* | (2006.01) |
| *A61K 8/34* | (2006.01) |
| *A61K 8/81* | (2006.01) |
| *A61K 8/894* | (2006.01) |
| *A61Q 5/10* | (2006.01) |

(52) U.S. Cl.
CPC ................ *A61K 8/585* (2013.01); *A61K 8/31* (2013.01); *A61K 8/34* (2013.01); *A61K 8/342* (2013.01); *A61K 8/58* (2013.01); *A61K 8/8147* (2013.01); *A61K 8/894* (2013.01); *A61Q 5/10* (2013.01); *A61K 2800/4324* (2013.01); *A61K 2800/884* (2013.01); *A61K 2800/95* (2013.01)

(58) Field of Classification Search
CPC . A61K 8/585; A61K 8/31; A61K 8/34; A61K 8/342; A61K 8/58; A61K 8/8147; A61K 8/894; A61K 2800/4324; A61K 2800/884; A61K 2800/95; A61Q 5/10
See application file for complete search history.

(56) References Cited

U.S. PATENT DOCUMENTS

| | | | |
|---|---|---|---|
| 2010/0083446 A1 | 4/2010 | Brun et al. | |
| 2010/0303748 A1* | 12/2010 | Hercouet | A61Q 5/10 8/405 |
| 2016/0235655 A1* | 8/2016 | Herrlein | A61Q 5/065 |
| 2018/0369108 A1* | 12/2018 | Daubresse | A61Q 5/12 |

FOREIGN PATENT DOCUMENTS

| | | |
|---|---|---|
| EP | 2168633 A2 | 3/2010 |
| FR | 2944964 A1 | 11/2010 |
| FR | 2944965 A1 | 11/2010 |
| FR | 3044902 A1 | 6/2017 |
| WO | 2011128309 A1 | 10/2011 |
| WO | 2013068979 A2 | 5/2013 |
| WO | 2017102854 A1 | 6/2017 |

* cited by examiner

*Primary Examiner* — Doan T Phan
(74) *Attorney, Agent, or Firm* — Lorenz & Kopf, LLP

(57) ABSTRACT

The object of the present disclosure is a method for treating keratinous material, in particular human hair, involving applying the following to the keratinous material
  a first composition (A) comprising, relative to the total weight of the composition (A)
    (A1) less than 10% by weight of water and
    (A2) one or more organic $C_1$-$C_6$ alkoxy silanes and/or their condensation products, and
  a second composition (B) comprising
    (B1) water and
    (B2) one or more terpenes.

20 Claims, No Drawings

METHOD FOR TREATING KERATIN MATERIAL

CROSS-REFERENCE TO RELATED APPLICATION

This application is a U.S. National-Stage entry under 35 U.S.C. § 371 based on International Application No. PCT/EP2020/054100, filed Feb. 17, 2020, which was published under PCT Article 21(2) and which claims priority to German Application No. 102019204807.2, filed Apr. 4, 2019, which are all hereby incorporated in their entirety by reference.

TECHNICAL FIELD

The present application is in the field of cosmetics and concerns a process for the treatment of keratinous material, in particular human hair, which comprises the use of two compositions (A) and (B). Composition (A) is a low-water preparation comprising at least one $C_1$-$C_6$ organic alkoxysilane, and composition (B) comprises at least one terpene in addition to water.

A second object of the present disclosure is a kit-of-parts for dyeing keratinous material, which comprises the two compositions (A) and (B) described above, separately packaged in two packaging units.

BACKGROUND

Changing the shape and color of keratinous fibers, especially hair, is an important area of modern cosmetics. To change the hair color, the specialist knows various coloring systems depending on the coloring requirements. Oxidation dyes are usually used for permanent, intensive colorations with good fastness properties and good grey coverage. Such dyes usually contain oxidation dye precursors, so-called developer components and coupler components, which form the actual dyes with one another under the influence of oxidizing agents, such as hydrogen peroxide. Oxidation dyes are exemplified by very long-lasting dyeing results.

When direct dyes are used, ready-made dyes diffuse from the colorant into the hair fiber. Compared to oxidative hair dyeing, the colorations obtained with direct dyes have a shorter shelf life and quicker wash ability. Dyeings with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting colorations, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair.

EP 2168633 B1 deals with the task of producing long-lasting hair colorations using pigments. It teaches that by using a combination of pigment, organic silicon compound, hydrophobic polymer and a solvent, it is possible to create colorations on hair that are particularly resistant to shampooing.

The organic silicon compounds used in EP 2168633 B1 are reactive compounds from the class of alkoxy silanes. These alkoxy silanes hydrolyze at high rates in the presence of water and form hydrolysis products and/or condensation products, depending on the amounts of alkoxy silane and water used in each case. The influence of the amount of water used in this reaction on the properties of the hydrolysis or condensation product are described, for example, in WO 2013068979 A2.

When these alkoxy silanes or their hydrolysis or condensation products are applied to keratinous material, a film or coating is formed on the keratinous material which completely envelops the keratinous material and in this way strongly influences the properties of the keratinous material. Possible areas of application include permanent styling or permanent shape modification of keratin fibers. In this process, the keratin fibers are mechanically shaped into the desired form and then fixed in this form by forming the coating described above. Another particularly suitable application is the coloring of keratin material. In this application, the coating or film is produced in the presence of a coloring compound, for example a pigment. The film colored by the pigment remains on the keratin material or the keratin fibers and results in surprisingly wash-resistant dyeing.

The great advantage of the alkoxy-silane based dyeing principle is that the high reactivity of this class of compounds allows a very fast coating. This means that extremely good dyeing results can be achieved after very short application periods of only a few minutes. In addition to these advantages, however, the high reactivity of alkoxy silanes also has some disadvantages.

Due to their high level of reactivity, the organic alkoxy silanes cannot be prepared together with larger amounts of water, since a large excess of water initiates immediate hydrolysis and subsequent polymerization. The polymerization that takes place during storage of the alkoxy silanes in aqueous medium manifests itself in a thickening or gelation of the aqueous preparation. This makes the preparations so highly viscous and gelatinous that they can no longer be applied evenly to the keratin material. In addition, storage of the alkoxy silanes in the presence of high amounts of water is associated with a loss of their reactivity, so that the formation of a resistant coating on the keratin material is also no longer possible.

BRIEF SUMMARY

Methods for treating keratinous material, and kits-of-parts for the same, are provided. In an exemplary embodiment, a method includes applying a first composition (A) and a second composition (B) to the keratinous material. The first composition (A) comprises less than about 10 weight % water, and one or more $C_1$-$C_6$ alkoxy silanes, and/or the condensation products of the alkoxy silanes. The second composition (B) comprises water and one or more terpenes. A Kit-of-parts is provided in another embodiment. The kit of parts includes a first container containing a first composition (A) and a second container containing a second composition (B). The first composition (A) comprises less than about 10 weight % water, and one or more $C_{1-6}$ alkoxy silanes, and/or the condensation products of the alkoxy silanes. The second composition (B) comprises water and one or more terpenes.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

For these reasons, it is necessary to store the organic alkoxy silanes in an anhydrous or anhydrous environment and to prepare the corresponding preparations in a separate container. Due to their high level of reactivity, alkoxy silanes can react not only with water but also with other cosmetic ingredients. In order to avoid all undesirable reactions, the preparations containing alkoxy silanes therefore preferably do not contain any other ingredients or contain only those selected ingredients which have proved to be chemically inert to the alkoxy silanes. Accordingly, the concentration of alkoxy silanes in the preparation is preferably chosen to be relatively high. The low-water preparations containing the alkoxy silanes in relatively high concentrations can also be referred to as "silane blends".

For application to the keratin material, the user must now convert this relatively highly concentrated silane blend into a ready-to-use mixture. In this ready-to-use mixture, on the one hand the concentration of organic alkoxy silanes is reduced, and on the other hand the application mixture also contains a higher proportion of water (or an alternative ingredient), which triggers the polymerization leading to the coating.

It has proved to be an extremely great challenge to optimally adapt the polymerization rate, i.e., the speed at which the coating forms on the keratin material, to the application conditions.

When applied to human hair, for example, a polymerization rate that is too fast will result in polymerization being completed before all sections of hair have been treated. Therefore, too fast polymerization makes the whole-head treatment impossible. In the dyeing process, the excessively fast polymerization manifests itself in an extremely uneven color result, so that the hair sections that were treated last are only poorly colored.

On the other hand, if polymerization is too slow, all areas of the hair can be treated without time pressure, but this increases the application time. Therefore, if polymerization is too slow, the great advantage of this dyeing technology, the formation of washfast colorations within shortest application periods, does not come into effect.

The object of the present application was to find a process for treating keratinous material by controlling the rate of polymerization of organic alkoxy-silanes could be adapted to the conditions of use, in particular to the conditions prevailing when applied to the human head. In other words, a process was sought by which the organic alkoxy-silanes would remain reactive long enough to permit whole-head treatment without unduly prolonging the application period.

Surprisingly, it has been found that this task can be fully solved if the keratin material is treated in a process in which two compositions (A) and (B) are applied to the keratin material. The first composition (A) is the low water silane blend described previously. The second composition (B) is hydrous and also contains at least one terpene. During application, both compositions (A) and (B) come into contact with each other, whereby this contact can be made either by prior mixing of (A) and (B) or by successive application of (A) and (B) to the keratin material.

A first object of the present disclosure is a method for treating keratinous material, in particular human hair, involving applying the following to the keratinous material
    a first composition (A) comprising, relative to the total weight of the composition (A)
        (A1) less than about 10% by weight of water and
        (A2) one or more organic $C_1$-$C_6$ alkoxy silanes and/or their condensation products, and
    a second composition (B) comprising
        (B1) water and
        (B2) one or more terpenes.

A first object of the present disclosure is a method for treating keratinous material, in particular human hair, involving applying the following to the keratinous material
    a first composition (A) comprising, relative to the total weight of the composition (A)
        (A1) less than about 10% by weight of water and
        (A2) one or more organic $C_1$-$C_6$ alkoxy silanes, and
    a second composition (B) comprising
        (B1) water and
        (B2) one or more terpenes.

It has been shown that the terpenes (B2) contained in the water-containing composition (B) reduce the polymerization rate of the $C_1$-$C_6$ organic alkoxy silanes (A2) upon contact with the composition (A). Surprisingly, the reactivity of the organic $C_1$-$C_6$ alkoxy silanes (A2) could thus be optimally adapted to the application conditions prevailing in a whole-head hair dyeing process. Even more complicated or time-consuming dyeing techniques, such as the dyeing of highlights specially arranged on the head, could be realized by using the method as contemplated herein. When the two compositions (A) and (B) were used in a dyeing process on keratinous material, in particular on human hair, it was possible in this way to obtain colorations with a particularly high degree of uniformity.

Treatment of Keratinous Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair in particular.

Agents for treating keratinous material are understood to mean, for example, agents for coloring the keratinous material, agents for reshaping or shaping keratinous material, in particular keratinous fibers, or agents for conditioning or caring for the keratinous material. The agents prepared by the process as contemplated herein are particularly suitable for dyeing keratinous material, in particular for dyeing keratinous fibers, which are preferably human hair.

The term "coloring agent" is used in the context of the present disclosure to refer to a coloring of the keratin material, in particular of the hair, caused by the use of coloring compounds, such as thermochromic and photochromic dyes, pigments, mica, direct dyes and/or oxidation dyes. In this staining process, the aforementioned colorant compounds are deposited in a particularly homogeneous and smooth film on the surface of the keratin material or diffuse into the keratin fiber. The film is formed in situ by oligomerization or polymerization of the organic alkoxy silane(s), and by the interaction of the colorant compound and organic silicon compound and optionally other components, such as a film-forming polymer.

Water Content (A1) in the Composition (A)

The process as contemplated herein is exemplified by the application of a first composition (A) to the keratinous material.

To ensure a sufficiently high storage stability, composition (A) is exemplified in that it is low in water, preferably substantially free of water. Therefore, the composition (A) contains less than about 10% by weight of water, based on the total weight of the composition (A).

With a water content of just under about 10% by weight, the compositions (A) are stable in storage over long periods. However, in order to further improve the storage stability and to ensure a sufficiently high reactivity of the organic $C_1$-$C_6$ alkoxy silanes (A2), it has been found to be particularly preferable to further lower the water content in the composition (A). For this reason, first composition (A) preferably contains about 0.01 to about 9.5% by weight, more preferably about 0.01 to about 8.0% by weight, still more preferably about 0.01 to about 6.0 and most preferably about 0.01 to about 4.0% by weight of water (A1), based on the total weight of composition (A).

In one particularly preferred version, a process as contemplated herein is exemplified in that the first composition (A) contains about 0.01 to about 9.5% by weight, preferably about 0.01 to about 8.0% by weight, more preferably about 0.01 to about 6.0 and most preferably about 0.01 to about 4.0% by weight of water (A1), based on the total weight of the composition (A).

Organic $C_1$-$C_6$ Alkoxy Silanes (A2) and/or their Condensation Products in the Composition (A)

The composition (A) is exemplified in that it comprises one or more organic $C_1$-$C_6$ alkoxy silanes (A2) and/or their condensation products.

The organic $C_1$-$C_6$ alkoxy silane(s) are organic, non-polymeric silicon compounds, preferably selected from the group of silanes containing one, two or three silicon atoms.

Organic silicon compounds, alternatively known as organosilicon compounds, are compounds that either have a direct silicon-carbon (Si—C) bond or in which the carbon is attached to the silicon atom via an oxygen, nitrogen or sulfur atom. The organic silicon compounds as contemplated herein are preferably compounds containing one to three silicon atoms. Organic silicon compounds preferably contain one or two silicon atoms.

According to IUPAC rules, the term silane stands for a group of chemical compounds based on a silicon skeleton and hydrogen. In organic silanes, the hydrogen atoms are completely or partially replaced by organic groups such as (substituted)alkyl groups and/or alkoxy groups.

Typically, the $C_1$-$C_6$ alkoxy silanes of the present disclosure have at least one $C_1$-$C_6$ alkoxy group bonded directly to a silicon atom. The $C_1$-$C_6$ alkoxy silanes as contemplated herein thus comprise at least one structural unit R'R''R'''Si—O—($C_1$-$C_6$ alkyl) where the radicals R', R'' and R'''' represent the three remaining bond valencies of the silicon atom.

The $C_1$-$C_6$ alkoxy group or groups bonded to the silicon atom are very reactive and are hydrolyzed at high rates in the presence of water, the rate of reaction depending, among other things, on the number of hydrolyzable groups per molecule. If the hydrolyzable $C_1$-$C_6$ alkoxy group is an ethoxy group, the organic silicon compound preferably contains a structural unit R'R''R'''Si—O—$CH_2$—$CH_3$. The residues R', R'' and R'''' again represent the three remaining free valences of the silicon atom.

Even the addition of small amounts of water leads first to hydrolysis and then to a condensation reaction between the organic alkoxy silanes. For this reason, both the organic alkoxy silanes (A2) and their condensation products may be present in the composition.

A condensation product is understood to be a product formed by the reaction of at least two organic $C_1$-$C_6$ alkoxy silanes with elimination of water and/or with elimination of a $C_1$-$C_6$ alkanol.

The condensation products can be, for example, dimers, but also trimers or oligomers, the condensation products being in equilibrium with the monomers.

Depending on the amount of water used or consumed in the hydrolysis, the equilibrium of monomeric $C_1$-$C_6$-alkoxysilane shifts towards the condensation product.

In a highly preferred version, a process as contemplated herein is exemplified in that the composition (A) comprises one or more organic $C_1$-$C_6$ alkoxy silanes (A2) selected from silanes having one, two or three silicon atoms, the organic silicon compound preferably further comprising one or more basic chemical functions.

This basic group can be, for example, an amino group, an alkylamino group or a dialkylamino group, which is preferably connected to a silicon atom via a linker. Preferably, the basic group is an amino group, a $C_1$-$C_6$ alkylamino group or a di($C_1$-$C_6$)alkylamino group.

A highly preferred method as contemplated herein is exemplified in that the composition (A) comprises one or more organic $C_1$-$C_6$ alkoxy silanes (A2) selected from the group of silanes having one, two or three silicon atoms, and wherein the $C_1$-$C_6$ alkoxy silanes further comprise one or more basic chemical functions.

Particularly good results were obtained when $C_1$-$C_6$ alkoxy silanes of formula (S-I) and/or (S-II) were used in the process as contemplated herein. Since, as previously described, hydrolysis/condensation already starts at trace amounts of moisture, the condensation products of the $C_1$-$C_6$ alkoxy silanes of formula (S-I) and/or (S-II) are also encompassed by this version.

In another highly preferred version, a process as contemplated herein is exemplified in that the first composition (A) comprises one or more organic $C_1$-$C_6$ alkoxy silanes (A2) of the formula (S-I) and/or (S-II), $$R_1R_2N\text{-}L\text{-}Si(OR_3)_a(R_4)_b \tag{S-I}$$

where $R_1$, $R_2$ independently represent a hydrogen atom or a $C_1$-$C_6$ alkyl group, L is a linear or branched divalent $C_1$-$C_{20}$ alkylene group, $R_3$, $R_4$ independently represent a $C_1$-$C_6$ alkyl group, a, stands for an integer from 1 to 3, and b is the integer 3-a, and $$(R_5O)_c(R_6)_d Si\text{-}(A)_e\text{-}[NR_7\text{-}(A')]_f\text{-}[O\text{-}(A'')]_g\text{-}[NR_8\text{-}(A''')]_h\text{-}Si(R_{6'})_{d'}(OR_{5'})_{c'} \tag{S-II},$$

where $R_5$, $R_{5'}$, $R_{5''}$, $R_6$, $R_{6'}$ and $R_{6''}$ independently represent a $C_1$-$C_6$ alkyl group, A, A', A'', A''' and A'''' independently represent a linear or branched $C_1$-$C_{20}$ divalent alkylene group, $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (S-III), $$(A'''')\text{-}Si(R_{6''})_{d''}\text{-}(OR_{5''})_{c''} \tag{S-III},$$

c, stands for an integer from 1 to 3, d stands for the integer 3-c, c' stands for an integer from 1 to 3, d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
provided that at least one of e, f, g and h is different from 0,
and/or their condensation products.

The substituents $R_1$, $R_2$, $R_3$, $R_4$, $R_5$, $R_{5'}$, $R_{5''}$, $R_6$, $R_{6'}$, $R_{6''}$, $R_7$, $R_8$, L, A, A', A", A''' and A'''' in the compounds of formula (S-I) and (S-II) are exemplified below: Examples of a $C_1$-$C_6$ alkyl group include methyl, ethyl, propyl, isopropyl, n-butyl, s-butyl and t-butyl, n-pentyl and n-hexyl groups. Propyl, ethyl and methyl are preferred alkyl radicals. Examples of a $C_2$-$C_6$ alkenyl group include vinyl, allyl, but-2-enyl, but-3-enyl, and isobutenyl; preferred $C_2$-$C_6$ alkenyl radicals include vinyl and allyl. Preferred examples of a hydroxy-$C_1$-$C_6$-alkyl group include a hydroxymethyl, a 2-hydroxyethyl, a 2-hydroxypropyl, a 3-hydroxypropyl, a 4-hydroxybutyl, a 5-hydroxypentyl and a 6-hydroxyhexyl group; a 2-hydroxyethyl group is particularly preferred. Examples of an amino-$C_1$-$C_6$-alkyl group include the aminomethyl group, the 2-aminoethyl group, the 3-aminopropyl group. The 2-aminoethyl group is particularly preferred. Examples of a linear divalent $C_1$-$C_{20}$ alkylene group include, for example, the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched $C_3$-$C_{20}$ divalent alkylene groups include (—$CH_2$—$CH(CH_3)$—) and (—$CH_2$—$CH(CH_3)$—$CH_2$—).

In the organic silicon compounds of the formula (S-I)

$R_1R_2N\text{-L-}Si(OR_3)_a(R_4)_b$ (S-I), $R_1$ and $R_2$ independently represent a hydrogen atom or a $C_1$-$C_6$ alkyl group. Most preferably,
$R_1$ and $R_2$ are both hydrogen atom.

In the middle part of the organic silicon compound is the structural unit or linker -L-which stands for a linear or branched, divalent $C_1$-$C_{20}$ alkylene group. The divalent $C_1$-$C_{20}$ alkylene group may alternatively be referred to as a divalent or divalent $C_1$-$C_{20}$ alkylene group, by which is meant that each -L- grouping may form two bonds.

Preferably, -L- represents a linear, divalent $C_1$-$C_{20}$ alkylene group. More preferred would be if -L- represents a linear divalent $C_1$-$C_6$ alkylene group. Particularly preferred would be if -L- represents a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Extremely preferred would be if L represents a propylene group (—$CH_2$—$CH_2$—$CH_2$—).

The organic silicon compounds as contemplated herein of the formula (S-I)

$R_1R_2N\text{-L-}Si(OR_3)_a(R_4)_b$ (S-I), each carry at one end the silicon-containing grouping —$Si(OR_3)_a(R_4)_b$.

In the terminal structural unit —$Si(OR_3)_a(R_4)_b$, $R_3$ and $R_4$ independently represent a $C_1$-$C_6$ alkyl group, particularly preferably $R_3$ and $R_4$ independently represent a methyl group or an ethyl group.

In this case, a stands for an integer from 1 to 3, and b stands for the integer 3-a. If a stands for the number 3, then b is equal to 0. If a stands for the number 2, then b is equal to 1. If a stands for the number 1, then b is equal to 2.

Keratin treatment agents with particularly good properties could be prepared if the composition (A) contains at least one organic $C_1$-$C_6$ alkoxy silane of the formula (S-I) in which the radicals $R_3$, $R_4$ independently of one another represent a methyl group or an ethyl group.

Furthermore, colorations with the best wash fastnesses could be obtained if the composition (A) contains at least one organic $C_1$-$C_6$ alkoxy silane of the formula (S-I) in which the radical a represents the number 3. In this case the rest b stands for the number 0.

In another preferred version, a process as contemplated herein is exemplified in that the composition (A) comprises one or more organic $C_1$-$C_6$ alkoxy silanes of formula (S-I), where $R_3$, $R_4$ independently represent a methyl group or an ethyl group, and a stands for the number 3 and b stands for the number 0.

In another preferred version, a process as contemplated herein is exemplified in that the composition (A) comprises at least one or more organic $C_1$-$C_6$ alkoxy silanes of formula (S-I),

$R_1R_2N\text{-L-}Si(OR_3)_a(R_4)_b$ (S-I), where $R_1$, $R_2$ both represent a hydrogen atom, and L is a linear, divalent $C_1$-$C_6$ alkylene group, preferably a propylene group (—$CH_2$—$CH_2$—$CH_2$—) or an ethylene group (—$CH_2$—$CH_2$—), $R_3$ represents an ethyl group or a methyl group, $R_4$ represents a methyl group or an ethyl group, a stands for the number 3 and b stands for the number 0.

Organic silicon compounds of the formula (I) which are particularly suitable for solving the problem as contemplated herein are (3-Aminopropyl)triethoxysilane

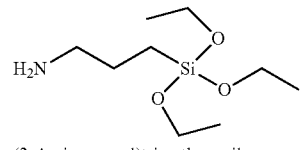

(3-Aminopropyl)trimethoxysilane

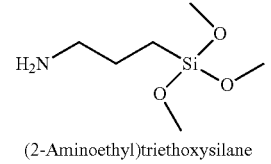

(2-Aminoethyl)triethoxysilane

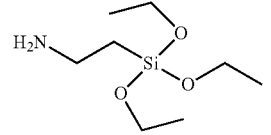

-continued (2-Aminoethyl)trimethoxysilane

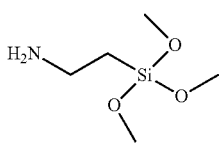

(3-Dimethylaminopropyl)triethoxysilane

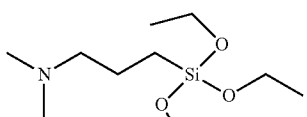

(3-Dimethylaminopropyl)trimethoxysilane

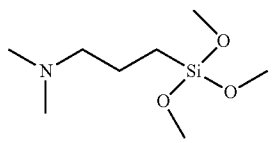

(2-Dimethylaminoethyl)triethoxysilane.

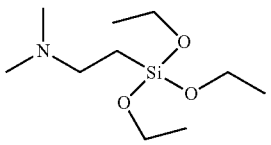

(2-Dimethylaminoethyl)trimethoxysilane and/or

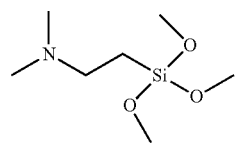

In a further preferred version, a process as contemplated herein is exemplified in that the first composition (A) comprises at least one $C_1$-$C_6$ organic alkoxysilane (A2) of formula (S-I) selected from the group of
(3-Aminopropyl)triethoxysilane
(3-Aminopropyl)trimethoxysilane
(2-Aminoethyl)triethoxysilane
(2-Aminoethyl)trimethoxysilane
(3-Dimethylaminopropyl)triethoxysilane
(3-Dimethylaminopropyl)trimethoxysilane
(2-Dimethylaminoethyl)triethoxysilane,
(2-Dimethylaminoethyl)trimethoxysilane
and/or their condensation products.

The aforementioned organic silicon compound of formula (I) is commercially available.
(3-aminopropyl)trimethoxysilane, for example, can be purchased from SIGMA-ALDRICH®.
(3-aminopropyl)triethoxysilane is also commercially available from SIGMA-ALDRICH®.

In another version of the method as contemplated herein, the composition (A) may also comprise one or more organic $C_1$-$C_6$ alkoxy silanes of formula (S-II),

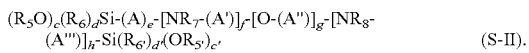
(S-II).

The organosilicon compounds of the formula (S-II) as contemplated herein each bear at their two ends the silicon-comprising groupings $(R_5O)_c(R_6)_dSi—$ and $—Si(R_{6'})_{d'}(OR_{5'})_{c'}$.

In the middle part of the molecule of formula (S-II) there are the groupings $-(A)_e-$ and $—[NR_7-(A')]_f-$ and $—[O-(A'')]_g-$ and $—[NR_8-(A''')]_h-$. Here, each of the radicals e, f, g and h can independently of one another stand for the number 0 or 1, with the proviso that at least one of the radicals e, f, g and h is different from 0. In other words, an organic silicon compound of formula (II) as contemplated herein contains at least one grouping selected from the group of $-(A)-$ and $—[NR_7-(A')]-$ and $—[O-(A'')]-$ and $—[NR_8-(A''')]-$.

In the two terminal structural units $(R_5O)_c(R_6)_dSi—$ and $—Si(R_{6'})_{d'}(OR_{5'})_{c'}$, the residues $R_5$, $R_{5'}$, $R_{5''}$ independently represent a $C_1$-$C_6$ alkyl group. The $R_6$, $R_{6'}$ and $R_{6''}$ residues independently represent a $C_1$-$C_6$ alkyl group.

Here c stands for an integer from 1 to 3, and d stands for the integer 3-c. If c stands for the number 3, then d is equal to 0. If c stands for the number 2, then d is equal to 1. If c stands for the number 1, then d is equal to 2.

Analogously c' stands for a whole number from 1 to 3, and d' stands for the whole number 3-c'. If c' stands for the number 3, then d' is 0. If c' stands for the number 2, then d' is equal to 1. If c' stands for the number 1, then d' is 2.

Colorations with the best wash fastness values could be obtained if the residues c and c' both stand for the number 3. In this case d and d' both stand for the number 0.

In another preferred version, a process as contemplated herein is exemplified in that the composition (A) comprises one or more organic $C_1$-$C_6$ alkoxy silanes of formula (S-II),

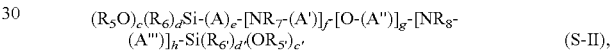
(S-II), where
$R_5$ and $R_{5'}$ independently represent a methyl group or an ethyl group,
c and c' both stand for the number 3 and
d and d' both stand for the number 0.

When c and c' are both 3 and d and d' are both 0, the organic silicon compounds as contemplated herein correspond to the formula (S-IIa)

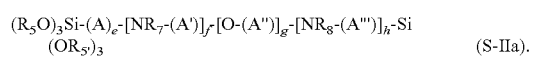
(S-IIa).

The radicals e, f, g and h may independently represent the number 0 or 1, with at least one of e, f, g and h being different from zero. The abbreviations e, f, g and h thus define which of the groupings $-(A)_e-$ and $—[NR_7-(A')]_f-$ and $—[O-(A'')]_g-$ and $—[NR_8-(A''')]_h-$ are in the middle part of the organic silicon compound of the formula (II).

In this context, the presence of certain groupings has proven to be particularly advantageous in terms of achieving washable dyeing results. Particularly good results were obtained when at least two of the residues e, f, g and h stand for the number 1. Especially preferred e and f both stand for the number 1. Furthermore, g and h both stand for the number 0.

When e and f are both 1 and g and h are both 0, the organic silicon compounds as contemplated herein correspond to the formula (S-IIb)

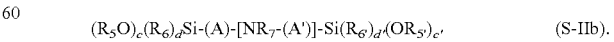
(S-IIb).

A, A', A'', A''' and A'''' independently represent a linear or branched $C_1$-$C_{20}$ divalent alkylene group. Preferably, A, A', A'', A''' and A'''' independently represent a linear divalent $C_1$-$C_{20}$ alkylene group. Further preferably, A, A', A'', A''' and A'''' independently represent a linear divalent $C_1$-$C_6$ alkylene group.

The divalent $C_1$-$C_{20}$ alkylene group may alternatively be referred to as a divalent $C_1$-$C_{20}$ alkylene group, by which is meant that each grouping A, A', A", A'" and A"" may form two bonds.

Particularly preferred would be if A, A', A", A'" and A"" independently represent a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). It would be extremely preferred if the radicals A, A', A", A'" and A"" represent a propylene group (—$CH_2$—$CH_2$—$CH_2$—).

When the radical f represents the number 1, the organic silicon compound of formula (II) as contemplated herein contains a structural grouping —[$NR_7$-(A')]-. When the radical h represents the number 1, the organic silicon compound of formula (II) as contemplated herein contains a structural grouping —[$NR_8$-(A'")]-.

Wherein $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (S-III)

  (S-III).

Very much preferred, $R_7$ and $R_8$ independently represent a hydrogen atom, a methyl group, a 2-hydroxyethyl group, a 2-alkenyl group, a 2-aminoethyl group or a group of formula (S-III).

When the radical f represents the number 1 and the radical h represents the number 0, the organic silicone compound as contemplated herein contains the grouping [$NR_7$-(A')], but does not contain the grouping —[$NR_8$-(A'")]. If the radical $R_7$ now stands for a grouping of the formula (III), the organic silicone compound comprises 3 reactive silane groups.

In another preferred version, a process as contemplated herein is exemplified in that the composition (A) comprises one or more organic $C_1$-$C_6$ alkoxy silanes (A2) of formula (S-II)

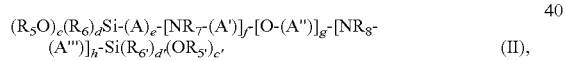   (II), where e and f both stand for the number 1, g and h both stand for the number 0, A and A' independently represent a linear divalent $C_1$-$C_6$ alkylene group and $R_7$ represents a hydrogen atom, a methyl group, a 2-hydroxyethyl group, a 2-alkenyl group, a 2-aminoethyl group or a group of the formula (S-III).

In a further preferred version, a process as contemplated herein is exemplified in that the composition (A) comprises one or more organic $C_1$-$C_6$ alkoxy silanes (A2) of formula (S-II), wherein e and f both stand for the number 1, g and h both stand for the number 0, A and A' independently represent a methylene group (—$CH_2$—), an ethylene group (—$CH_2$—$CH_2$—) or a propylene group (—$CH_2$—$CH_2$—$CH_2$), and $R_7$ represents a hydrogen atom, a methyl group, a 2-hydroxyethyl group, a 2-alkenyl group, a 2-aminoethyl group or a group of the formula (S-III).

Organic silicon compounds of the formula (S-II) which are well suited for solving the problem as contemplated herein are 3-(trimethoxysilyl)-N-[3-(trimethoxysilyl)propyl]-1-propanamine

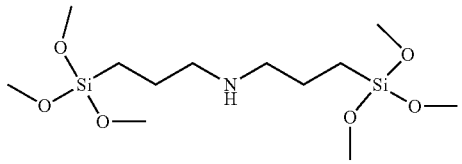

3-(Triethoxysilyl)-N-[3-(triethoxysilyl)propyl]-1-propanamine

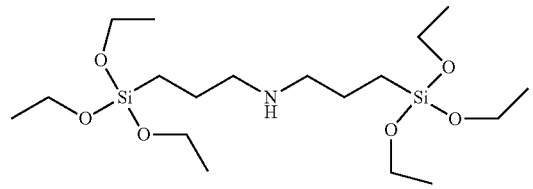

N-methyl-3-(trimethoxysilyl)-N-[3-(trimethoxysilyl)propyl]-1-propanamine

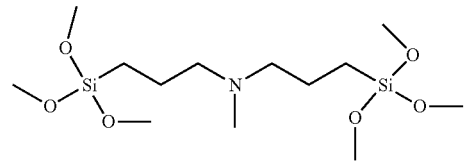

N-Methyl-3-(triethoxysilyl)-N-[3-triethoxysilyl)propyl]-1-propanamine

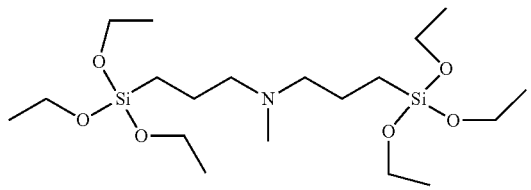

2-[Bis[3-(trimethoxysily)propyl]amino]-ethanol

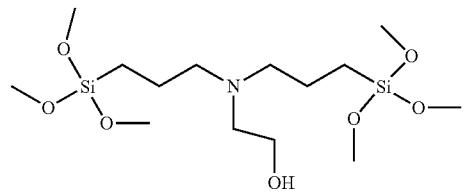

2-[bis[3-(triethoxysilyl)propyl]amino]ethanol

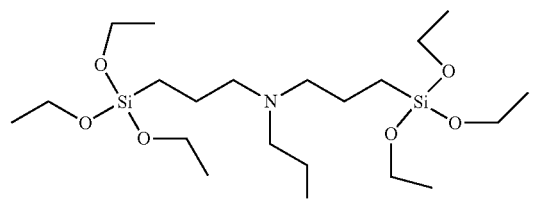

3-(Trimethoxysilyl)-N,N-bis[3-(trimethoxysilyl)propyl]-1-propanamine

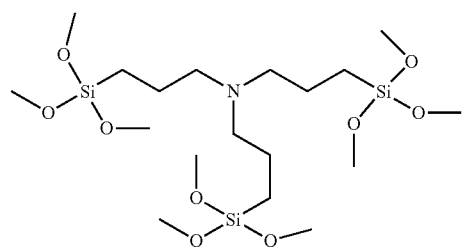

-continued 3-(Triethoxysilyl)-N,N-bis[3-(triethoxysilyl)propyl]-1-propanamine

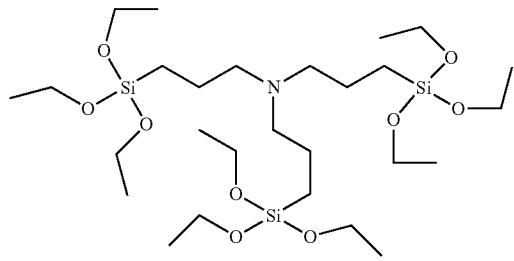

N1,N1-Bis[3-(trimethoxysilyl)propyl]-1,2-ethanediamine

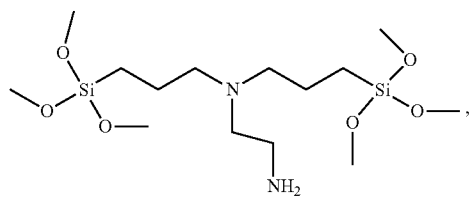

N1,N1-Bis[3-(triethoxysilyl)propyl]-1,2-ethanediamine

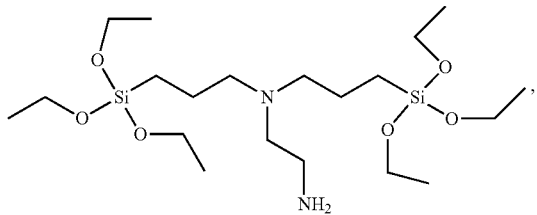

N,N-Bis[3-(trimethoxysilyl)propyl]-2-propen-1-amine

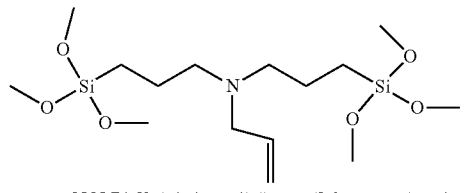

N,N-Bis[3-(triethoxysilyl)propyl]-2-propen-1-amine

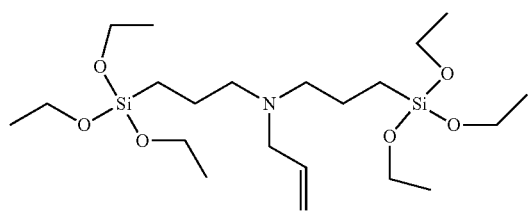

The aforementioned organic silicon compounds of formula (S-II) are commercially available.

Bis(trimethoxysilylpropyl)amines with the CAS number 82985-35-1 can be purchased from SIGMA-ALDRICH®.

Bis[3-(triethoxysilyl)propyl]amines with the CAS number 13497-18-2 can be purchased from SIGMA-ALDRICH®, for example.

N-methyl-3-(trimethoxysilyl)-N-[3-(trimethoxysilyl)propyl]-1-propanamine is alternatively referred to as bis(3-trimethoxysilylpropyl)-N-methylamine and can be purchased commercially from SIGMA-ALDRICH® or FLUOROCHEM®.

3-(triethoxysilyl)-N,N-bis[3-(triethoxysilyl)propyl]-1-propanamine with the CAS number 18784-74-2 can be purchased for example from FLUOROCHEM® or SIGMA-ALDRICH®.

In another preferred version, a process as contemplated herein is exemplified in that the composition (A) comprises one or more organic $C_1$-$C_6$ alkoxy silanes of formula (S-II) selected from the group of 3-(trimethoxysilyl)-N-[3-(trimethoxysilyl)propyl]-1-propanamine 3-(Triethoxysilyl)-N-[3-(triethoxysilyl)propyl]-1-propanamine N-methyl-3-(trimethoxysilyl)-N-[3-(trimethoxysilyl)propyl]-1-propanamine N-Methyl-3-(triethoxysilyl)-N-[3-(triethoxysilyl)propyl]-1-propanamine 2-[Bis[3-(trimethoxysilyl)propyl]amino]-ethanol 2-[bis[3-(triethoxysilyl)propyl]amino]ethanol 3-(Trimethoxysilyl)-N,N-bis[3-(trimethoxysilyl)propyl]-1-propanamine 3-(Triethoxysilyl)-N,N-bis[3-(triethoxysilyl)propyl]-1-propanamine N1,N1-bis[3-(trimethoxysilyl)propyl]-1,2-ethanediamine, N1,N1-bis[3-(triethoxysilyl)propyl]-1,2-ethanediamine, N,N-bis[3-(trimethoxysilyl)propyl]-2-propen-1-amine and/or N,N-bis[3-(triethoxysilyl)propyl]-2-propen-1-amine.

and/or their condensation products.

In further dyeing experiments, it has also been found to be highly advantageous if at least one organic $C_1$-$C_6$ alkoxy silane (A2) of the formula (S-IV) was used in the process as contemplated herein.

$$R_9Si(OR_{10})_k(R_{11})_m \quad \text{(S-IV)}.$$

The compounds of formula (S-IV) are organic silicon compounds selected from silanes having one, two or three silicon atoms, wherein the organic silicon compound comprises one or more hydrolysable groups per molecule.

The organic silicon compound(s) of formula (S-IV) may also be referred to as silanes of the alkyl-$C_1$-$C_6$-alkoxy-silane type, $$R_9Si(OR_{10})_k(R_{11})_m \quad \text{(S-IV),}$$

where $R_9$ represents a $C_1$-$C_{12}$ alkyl group, $R_{10}$ stands for a $C_1$-$C_6$ alkyl group, $R_{11}$ stands for a $C_1$-$C_6$ alkyl group k is an integer from 1 to 3, and m stands for the integer 3-k.

In a further version, a particularly preferred method as contemplated herein is exemplified in that the first composition (A) comprises one or more organic $C_1$-$C_6$ alkoxy silanes (A2) of the formula (S-IV), $$R_9Si(OR_{10})_k(R_{11})_m \quad \text{(S-IV),}$$

where $R_9$ represents a $C_1$-$C_{12}$ alkyl group, $R_{10}$ stands for a $C_1$-$C_6$ alkyl group, $R_{11}$ stands for a $C_1$-$C_6$ alkyl group k is an integer from 1 to 3, and m stands for the integer 3-k.

and/or their condensation products.

In the organic $C_1$-$C_6$ alkoxy silanes of formula (S-IV), the $R_9$ radical represents a $C_1$-$C_{12}$ alkyl group. This $C_1$-$C_{12}$ alkyl group is saturated and can be linear or branched. Preferably, $R_9$ represents a linear $C_1$-$C_8$ alkyl group. Preferably, $R_9$ represents a methyl group, an ethyl group, an n-propyl group, an n-butyl group, an n-pentyl group, an n-hexyl group, an n-octyl group, or an n-dodecyl group. Especially preferred, $R_9$ represents a methyl group, an ethyl group or an n-octyl group.

In the organic silicon compounds of formula (S-IV), the radical $R_{10}$ represents a $C_1$-$C_6$ alkyl group. Especially preferred, $R_{10}$ stands for a methyl group or an ethyl group.

In the organic silicon compounds of the formula (S-IV), the radical Rn represents a $C_1$-$C_6$ alkyl group. In particular, $R_{11}$ stands for a methyl group or an ethyl group.

Furthermore k stands for a whole number from 1 to 3, and m stands for the whole number 3-k. If k stands for the number 3, then m is equal to 0. If k stands for the number 2, then m is equal to 1. If k stands for the number 1, then m is equal to 2.

Colorations with the best wash fastnesses were obtained when the composition (A) comprises at least one organic $C_1$-$C_6$ alkoxy silane (A2) of the formula (S-IV) in which the radical k represents the number 3. In this case the rest m stands for the number 0.

Organic silicon compounds of the formula (S-IV) which are particularly suitable for solving the problem as contemplated herein are Methyltrimethoxysilane

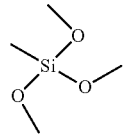

Methyltriethoxysilane

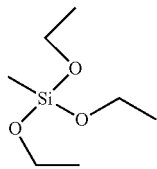

Ethyltrimethoxysilane

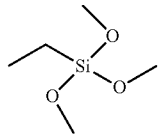

Ethyltriethoxysilane

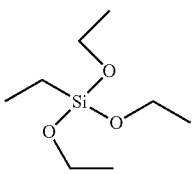

n-Propyltrimethoxysilane (also known as propyltrimethoxysilane)

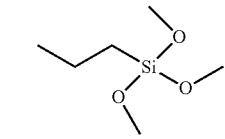

n-Propyltriethoxysilane (also known as propyltriethoxysilane)

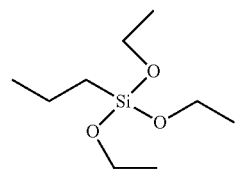

n-Hexyltrimethoxysilane (also known as hexyltrimethoxysilane)

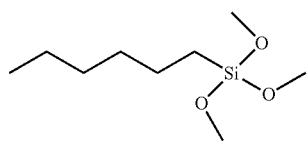

n-Hexyltriethoxysilane (also known as hexyltriethoxysilane)

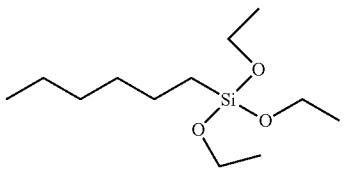

n-Octyltrimethoxysilane (also known as octyltrimethoxysilane)

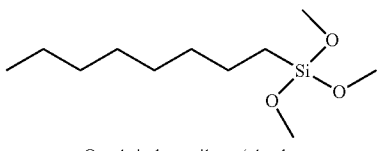

n-Octyltriethoxysilane (also known as octyltriethoxysilane)

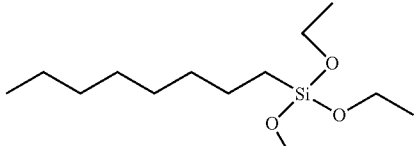

n-Dodecyltrimethoxysilane (also known as dodecyltrimethoxysilane) and/or

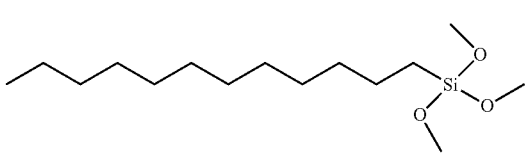

n-Dodecyltriethoxysilane (also known as dodecyltriethoxysilane)

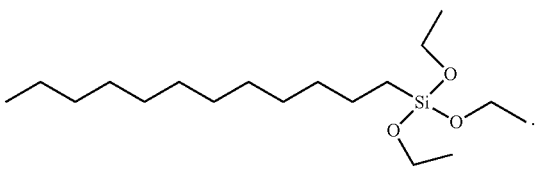

In a further preferred version, a process as contemplated herein is exemplified in that the first composition (A) comprises at least one $C_1$-$C_6$ organic alkoxysilane (A2) of formula (S-IV) selected from the group of
Methyltrimethoxysilane
Methyltriethoxysilane
Ethyltrimethoxysilane
Ethyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane.
and/or their condensation products.

The corresponding hydrolysis or condensation products are, for example, the following compounds:

hydrolysis of $C_1$-$C_6$ alkoxy silane of the formula (S-I) with water (reaction scheme using the example of 3-aminopropyltriethoxysilane):

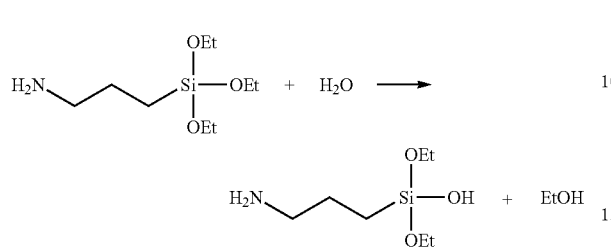

depending on the amount of water used, the hydrolysis reaction can also take place several times per $C_1$-$C_6$ alkoxy silane used

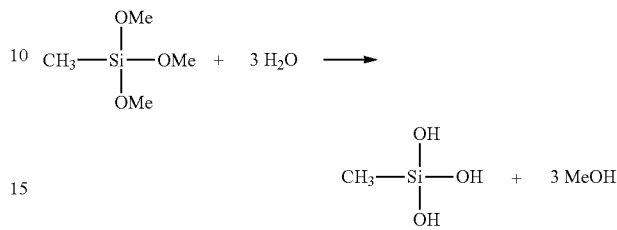

hydrolysis of $C_1$-$C_6$ alkoxy silane of the formula (S-IV) with water (reaction scheme using the example of methyltrimethoxysilane):

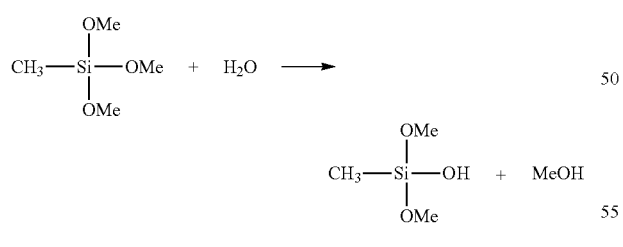

depending on the amount of water used, the hydrolysis reaction can also take place several times per $C_1$-$C_6$ alkoxy silane used

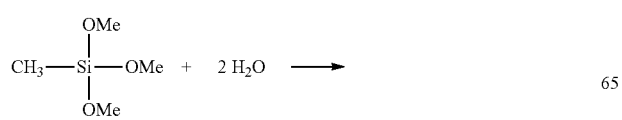

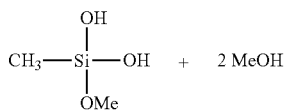

or

Possible condensation reactions are for example (shown by the mixture of (3-aminopropyl)triethoxysilane and methyltrimethoxysilane):

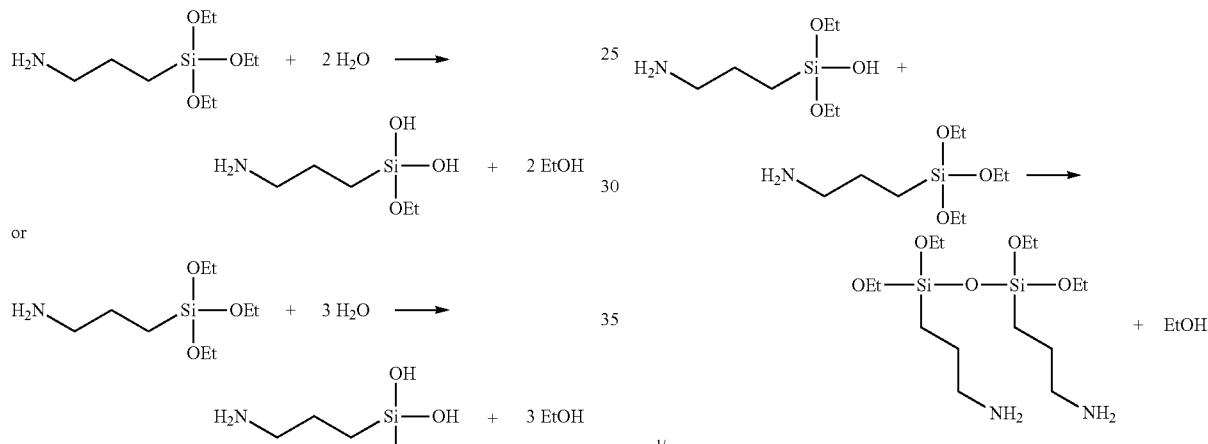

and/or

-continued

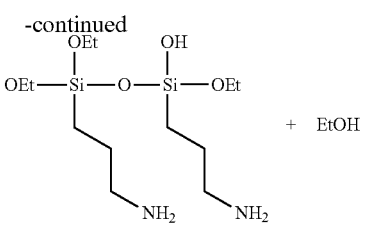

+ EtOH and/or

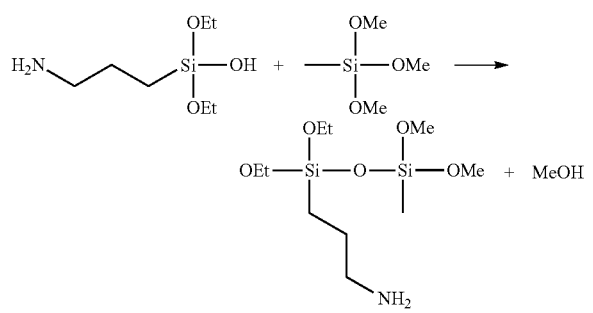

+ MeOH and/or

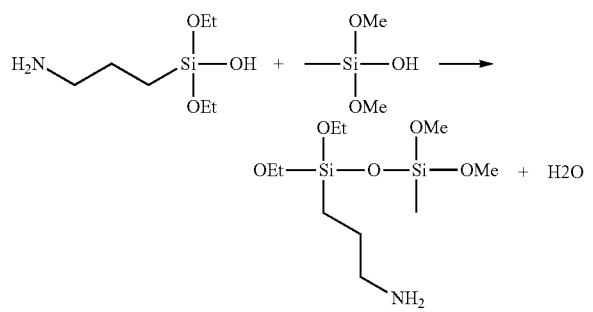

+ H2O and/or

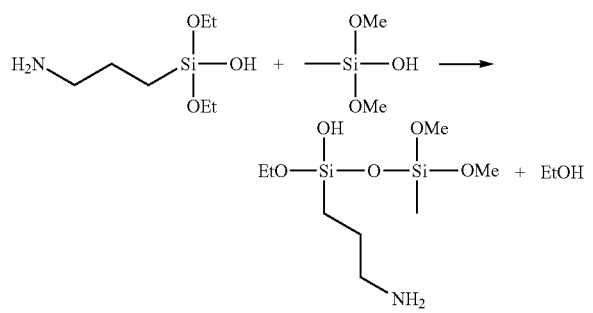

+ EtOH and/or

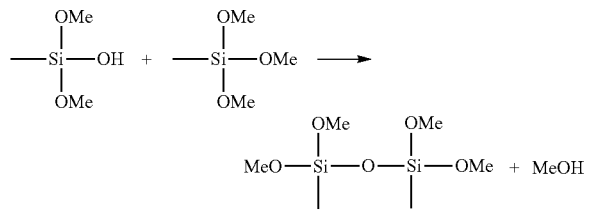

+ MeOH

In the above exemplary reaction schemes the condensation to a dimer is shown in each case, but further condensations to oligomers with several silane atoms are also possible and also preferred.

Both partially hydrolyzed and completely hydrolyzed $C_1$-$C_6$-alkoxysilanes of the formula (S-I) can participate in these condensation reactions, which undergo condensation with partially or also completely hydrolyzed $C_1$-$C_6$-alkoxysilanes of the formula (S-I) which have not yet reacted. In this case, the $C_1$-$C_6$ alkoxysilanes of formula (S-I) react with themselves.

Furthermore, both partially hydrolyzed and completely hydrolyzed $C_1$-$C_6$-alkoxysilanes of the formula (S-I) can also participate in the condensation reactions, which undergo condensation with not yet reacted, partially or also completely hydrolyzed $C_1$-$C_6$-alkoxysilanes of the formula (S-IV). In this case, the $C_1$-$C_6$ alkoxysilanes of formula (S-I) react with the $C_1$-$C_6$ alkoxysilanes of formula (S-IV).

Furthermore, both partially hydrolyzed and completely hydrolyzed $C_1$-$C_6$-alkoxysilanes of the formula (S-IV) can also participate in the condensation reactions, which undergo condensation with not yet reacted, partially or also completely hydrolyzed $C_1$-$C_6$-alkoxysilanes of the formula (S-IV). In this case, the $C_1$-$C_6$ alkoxysilanes of formula (S-IV) react with themselves.

The composition (A) as contemplated herein may comprise one or more organic $C_1$-$C_6$ alkoxysilanes (A2) in various proportions. This is determined by the expert depending on the desired thickness of the silane coating on the keratin material and the amount of keratin material to be treated.

Particularly storage-stable preparations with very good dyeing results in use could be obtained if the composition (A) contains—based on its total weight—one or more organic $C_1$-$C_6$-alkoxysilanes (A2) and/or the condensation products thereof in a total amount of from about 30.0 to about 85.0% by weight, preferably from about 35.0 to about 80.0% by weight, more preferably from about 40.0 to about 75.0% by weight, still more preferably from about 45.0 to about 70.0% by weight and highly preferably from about 50.0 to about 65.0% by weight.

In a further version, a highly preferred process is exemplified in that the first composition (A) comprises—based on the total weight of the composition (A)—one or more organic $C_1$-$C_6$ alkoxysilanes (A2) and/or the condensation products thereof in a total amount of from about 30.0 to about 85.0% by weight, preferably from about 35.0 to about 80.0% by weight, more preferably from about 40.0 to about 75.0% by weight, still more preferably from about 45.0 to about 70.0% by weight, and highly preferably from about 50.0 to about 65.0% by weight.

Other Cosmetic Ingredients in the Composition (A)

In principle, the composition (A) may also comprise one or more further cosmetic ingredients.

The cosmetic ingredients which may be optionally used in the composition (A) may be any suitable ingredients to impart further beneficial properties to the product. For example, the composition (A) may contain a solvent, a thickening or film-forming polymer, a surface-active compound from the group of nonionic, cationic, anionic or zwitterionic/amphoteric surfactants, coloring compounds from the group of pigments, direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

The selection of these other substances will be made by the specialist according to the desired properties of the agents. With regard to other optional components and the quantities of these components used, explicit reference is made to the relevant manuals known to the specialist.

However, as described previously, the organic $C_1$-$C_6$ alkoxysilanes (A2) can react not only with water but also with other cosmetic ingredients. To avoid these undesirable reactions, the preparations (A) with alkoxy silanes therefore preferably contain no other ingredients or only the selected ingredients which have proved to be chemically inert to the $C_1$-$C_6$ alkoxy silanes. In this context, it has proved particularly preferred to use in composition (A) a cosmetic ingredient selected from the group of hexamethyldisiloxane, octamethyltrisiloxane, decamethyltetrasiloxane, hexamethylcyclotrisiloxane, octamethylcyclotetrasiloxane and/or decamethylcyclopentasiloxane.

In another particularly preferred version, a process as contemplated herein is exemplified in that the first composition (A) comprises at least one cosmetic ingredient selected from the group of hexamethyldisiloxane, octamethyltrisiloxane, decamethyltetrasiloxane, hexamethylcyclotrisiloxane, octamethylcyclotetrasiloxane and decamethylcyclopentasiloxane. Hexamethyldisiloxane has the CAS number 107-46-0 and can be purchased commercially from SIGMA-ALDRICH®, for example.

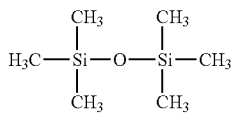

Octamethyltrisiloxane has the CAS number 107-51-7 and is also commercially available from SIGMA-ALDRICH®.

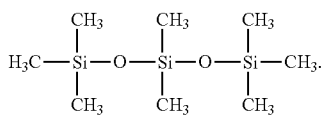

Decamethyltetrasiloxane has the CAS number 141-62-8 and is also commercially available from SIGMA-ALDRICH®.

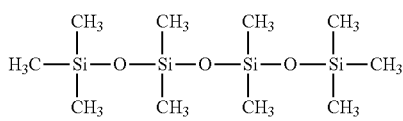

Hexamethylcyclotrisiloxane has the CAS No 541-05-9.
Octamethylcyclotetrasiloxane has the CAS No 556-67-2.
Decamethylcyclopentasiloxane has the CAS No 541-02-6.

The use of hexamethyldisiloxane in composition (A) has been found to be particularly preferred. Particularly preferably, hexamethyldisiloxane is present—based on the total weight of composition (A)—in amounts of about 10.0 to about 50.0% by weight, preferably about 15.0 to about 45.0% by weight, further preferably about 20.0 to about 40.0% by weight, still further preferably about 25.0 to about 35.0% by weight and most preferably about 31.0 to about 34.0% by weight in composition (A).

In a further particularly preferred version, a method is exemplified in that the first composition (A) contains—based on the total weight of the composition (A)—about 10.0 to about 50.0% by weight, preferably about 15.0 to about 45.0% by weight, further preferably about 20.0 to about 40.0% by weight, still further preferably about 25.0 to about 35.0% by weight and highly preferably about 31.0 to about 34.0% by weight of hexamethyldisiloxane.

Water Content (B1) in the Composition (B)

Typical of the process as contemplated herein is the application of a second composition (B) to the keratinous material, in particular to human hair.

When applied to the keratinous material, compositions (A) and (B) come into contact, this contact being particularly preferably established by prior mixing of the two compositions (A) and (B). Mixing (A) and (B) produces the keratin treatment agent ready for use, i.e. the silane blend (A) which is stable or capable of being stored is converted into its reactive form by contact with (B). Mixing of compositions (A) and (B) starts a polymerization reaction originating from the alkoxy-silane monomers or alkoxy-silane oligomers, which finally leads to the formation of the film or coating on the keratin material.

The more water comes into contact with the organic $C_1$-$C_6$ alkoxy silane(s), the greater the extent of the polymerization reaction. For example, if the composition (B) contains a lot of water, the monomeric or oligomeric silane condensates previously present in the low-water composition (A) now polymerize very rapidly to form polymers of higher or high molecular weight. The high molecular weight silane polymers then form the film on the keratinous material. For this reason, water (B1) is an essential ingredient of the present disclosure of composition (B).

The amount of water in the composition (B) can help determine the polymerization rate of the $C_1$-$C_6$ organic alkoxy silanes (A2) at the time of application. In order to ensure an even color result when dyeing the entire head, the polymerization speed, i.e., the speed at which the coating is formed, should not be too high. For this reason, it has been found to be particularly preferable not to select too high a quantity of water in composition (B).

Particularly uniform colorations on the entire head could be obtained if the composition (B)—based on the total weight of the composition (B)—contains about 5.0 to about 90.0% by weight, preferably about 15.0 to about 85.0% by weight, more preferably about 25.0 to about 80.0% by weight, still more preferably about 35.0 to about 75.0% by weight and highly preferably about 45.0 to about 70.0% by weight of water (B1).

In another particularly preferred version, a process as contemplated herein is exemplified in that the second composition (B) comprises—based on the total weight of the composition (B)—from about 5.0 to about 90.0% by weight, preferably from about 15.0 to about 85.0% by weight, more preferably from about 25.0 to about 80.0% by weight, still more preferably from about 35.0 to about 75.0% by weight, and highly preferably from about 45.0 to about 70.0% by weight of water (B1).

Terpenes in the Composition (B)

The composition (B) is further exemplified by its content of at least one terpene (B2). Surprisingly, it has been found that the use of at least one terpene (B2) optimizes the reaction rate of the organic $C_1$-$C_6$ alkoxy silanes in such a way as to allow uniform coloring over the entire head.

For the purposes of the present disclosure, a terpene is understood to be a natural substance having a carbon atom content which is a multiple of 5. Terpenes, mainly mono-, sesqui- and diterpenes, can be obtained from plants (or parts of plants) or essential oils by physical methods such as steam distillation, extraction or chromatography. Their carbon number is divisible by 5. The association with the terpenes is based on a common biosynthesis and the C5 rule, since the common building block of all terpenes is isoprene (2-methylbuta-1,3-diene).

In other words, a method of treating keratinous material, in particular human hair, is particularly preferred, in which there are applied to the keratinous material a first composition (A) comprising, relative to the total weight of the composition (A)
(A1) less than about 10% by weight of water and
(A2) one or more organic $C_1$-$C_6$ alkoxy silanes and/or their condensation products, and a second composition (B) comprising
(B1) water and
(B2) one or more terpenes derived from isoprene (2-methylbuta-1,3-diene).

The terpenes are included as part of the secondary plant substances. In general, a distinction is made between acyclic, mono-, bi-, tri-, tetra- and pentacyclic terpenes, i.e., molecules without, with one, with two, three, four or five rings. A terpene is understood to mean in particular all terpenes from the group of monoterpenes with 10 carbon atoms, sesquiterpenes with 15 carbon atoms and diterpenes with 20 carbon atoms.

In another particularly preferred version, a process as contemplated herein is exemplified in that the second composition (B) comprises one or more terpenes (B2) selected from the group of monoterpenes having 10 carbon atoms, sesquiterpenes having 15 carbon atoms and diterpenes having 20 carbon atoms.

Monoterpenes with 10 carbon atoms are understood to be all terpenes from the group of hydrocarbons, alcohols, glycosides, ethers, aldehydes, ketones, carboxylic acids and esters with 10 carbon atoms.

Sesquiterpenes with 15 carbon atoms are understood to be all terpenes from the group of hydrocarbons, alcohols, glycosides, ethers, aldehydes, ketones, carboxylic acids and esters with 15 carbon atoms.

Diterpenes with 20 carbon atoms are understood to be all terpenes from the group of hydrocarbons, alcohols, glycosides, ethers, aldehydes, ketones, carboxylic acids and esters with 20 carbon atoms.

In other words, a method of treating keratinous material, in particular human hair, is particularly preferred, in which there are applied to the keratinous material a first composition (A) comprising, relative to the total weight of the composition (A)
(A1) less than about 10% by weight of water and
(A2) one or more organic $C_1$-$C_6$ alkoxy silanes and/or their condensation products, and a second composition (B) comprising
(B1) water and
(B2) one or more terpenes selected from the group of monoterpenes containing 10 carbon atoms, sesquiterpenes containing 15 carbon atoms and diterpenes containing 20 carbon atoms.

In the systematics of organic chemistry, terpenes belong to the lipids and are thus hydrophobic compounds. Hydrophobic substances can form emulsions in the presence of water, forming micelle systems. Without being committed to this theory, it is believed that the $C_1$-$C_6$ alkoxysilanes—either in the form of their monomers or, optionally, in the form of their fused oligomers—are embedded in this hydrophobic environment or in the micelle systems so that the polarity of their environment changes. Due to the hydrophobic nature of the terpenes, the environment of the $C_1$-$C_6$ alkoxysilanes is also hydrophobized. It is assumed that the polymerization reaction of the $C_1$-$C_6$ alkoxy silanes leading to the film or coating takes place at a reduced rate in a hydrophobic environment. To produce particularly good results, very specific terpenes can be used preferentially in composition (B).

For example, limonene may be used as an explicitly highly preferred monoterpene. Limonene is a monoterpene with the molecular formula $C_{10}H_{16}$ and is alternatively known as 1-methyl-4-prop-1-en-2-yl-cyclohexene, Carven, or 1-methyl-4-isopropenyl-1-cyclohexene. Limonene occurs in the form of two enantiomers, (R)-(+)-limonene (also known as D-(+)-limonene or (+)-limonene for short) and (S)-(–)-limonene (also known as L-(–)-limonene or (–)-limonene for short). The racemate of the two enantiomers is also called dipentene. The CAS numbers of limonene are 7705-14-8 [(±)-limonene], 138-86-3 [dipentene unspecified] and 6876-12-6 [trans-1-methyl-4-(methylvinyl)cyclohexene]. All stereoisomers are contemplated herein.

Limonene is commercially distributed, for example, in the form of a limonene oil with the INCI designation CITRUS MEDICA LIMONUM (LEMON) PEEL OIL by F.LLi di Barolo S.r.L. D-Limonene can also be purchased from Brenntag Hungaria.

Citronellol can be used as a further particularly preferred monoterpene. Citronellol, 3,7-dimethyloct-6-en-1-ol, is an acyclic monoterpene with the molecular formula $C_{10}H_{20}O$. The compound contains a stereocenter, so that two enantiomers exist. They appear as colorless to pale yellow liquids which differ in odor. (R)-Citronellol has the smell of citronella oil, (S)-Citronellol smells like geranium oil. Citronellol has the CAS numbers 106-22-9 [(RS)-citronellol], 1117-61-9 [(R)-(+)-citronellol] and 7540-51-4 [(S)-(–)-citronellol]. All stereoisomers of citronellol are contemplated herein.

Citronellol is commercially sold, for example, by the manufacturer Novachem Aromatici (C.P. Essenze S.r.L.) or by the manufacturer Privi Organics Limited (Lansdowne Chemicals)

Geraniol may also be used as another highly preferred monoterpene. Geraniol is an acyclic monoterpene with the molecular formula $C_{10}H_{18}O$. Geraniol may alternatively be referred to as 2,6-dimethyl-trans-2,6-octadien-8-ol, or 3,7-dimethyl-trans-2,6-octadien-1-ol, or (E)-3,7-dimethyl-2,6-octadien-1-ol and bears CAS number 106-24-1. As a floral note, geraniol is a component of many perfumes.

Linalool can also be used as a further particularly preferred monoterpene. Linalool belongs to the acyclic monoterpenes and has the molecular formula $C_{10}H_{18}O$. Linalool may alternatively be expressed as 3,7-dimethyl-1,6-octadien-3-ol, (RS)-3,7-dimethyl-1,6-octadien-3-ol, rac-3,7-dimethyl-1,6-octadien-3-ol, (±)-3,7-dimethyl-1,6-octadien-3-ol, (RS)-(±)-linalool or linalyl alcohol. The substance has a stereogenic center at the carbon atom of position 3 and thus occurs in the form of two enantiomers. One enantiomer of linalool smells soapy-coriander-like, the second enantiomer smells woody-lavender-like. The smell of Racemate is described as a pleasant, slightly refreshing, floral/woody/tart smell. The CAS numbers of linalool are 78-70-6 (racemate), 126-91-06 [(R)-(–)-linalool] and 126-90-9 [(S)-(+)-linalool]. All stereoisomers of citronellol are contemplated herein.

Linalool is sold commercially under the trade name E260 by DSM.

Citral may also be used as another highly preferred monoterpene. Citral is the mixture of the cis-trans isomers geranial (citral A) and neral (citral B). Citral is the main component of lemongrass oil. Citral is an acyclic monoterpene with the molecular formula $C_{10}H_{16}O$. Citral may alternatively be referred to as 3,7-dimethylocta-2,6-dienal or (E)-3,7-dimethylocta-2,6-dienal (Geranial) or (Z)-3,7-dimethylocta-2,6-dienal (Neral). The CAS numbers of citral are 5392-40-5 (citral), 106-26-3 (neral) and 141-27-5 (geranial). All isomers of citral are contemplated herein.

Citronellal may also be used as another highly preferred monoterpene. Citronellal is an acyclic monoterpene with the molecular formula $C_{10}H_{18}O$. Alternative names for citronellal are rhodinal and 3,7-dimethyl-6-octen-1-al. Citronellal has the CAS number 106-23-0.

Citronellal is sold commercially by BASF®, for example.

Myrcene may also be used as another highly preferred monoterpene. Myrcene is an acyclic monoterpene with the molecular formula $C_{10}H_{16}$. Alternatively, myrcene may be referred to as 7-methyl-3-methylene-1,6-octadiene or as β-myrcene. Myrcene has the CAS number 123-35-3.

Carvone may also be used as a particularly preferred monoterpene. Carvone is a monocyclic monoterpene ketone and has the molecular formula C10H14O. Alternatively, carvone may be referred to as p-mentha-6,8-dien-2-one or 1-methyl-4-isopropenyl-6-cyclohexen-2-one. There are two enantiomeric carvones, the (S)-(+)-carvone [also known as D-(+)-carvone or (+)-carvone for short] and the (R)-(−)-carvone [also known as L-(−)-carvone or (−)-carvone for short]. Carvone has the CAS numbers 99-49-0 (racemate), 2244-16-8 and 6485-40-1. All stereoisomers of the carvone are contemplated herein.

As another particularly preferred monoterpene, α-terpinene may also be used. Alpha-terpinene is a naturally occurring chemical compound that is present in the form of a colorless, lemony-scented oil found in tea tree oil and nutmeg, as well as in numerous essential oils of other spice plants. α-Terpinene is a cyclic monoterpenic hydrocarbon with the molecular formula $C_{10}H_{16}$. Alpha-terpinene may alternatively be referred to as mentha-1,3-diene or 1-isopropyl-4-methyl-1,3-cyclohexadiene and has the CAS number 99-86-5.

Menthol may also be used as another particularly preferred monoterpene. Menthol is a monocyclic monoterpene alcohol with the molecular formula $C_{10}H_{20}O$. Menthol may alternatively be referred to as 2-isopropyl-5-methylcyclohexanol or as 5-methyl-2-(propan-2-yl)-cyclohexan-1-ol. Menthol has the CAS numbers 2216-51-5 [(−)-menthol, levomenthol], 89-78-1 [(±)-menthol, DL-menthol, racementhol], 15356-60-2 [(+)-menthol] and 1490-04-6 (menthol). All isomers of menthol are contemplated herein. It exists in two mirror-image forms, (−)-menthol (levomenthol) and (+)-menthol.

Pinenes can also be used as additional particularly preferred monoterpenes. Pinenes are monoterpene hydrocarbons with the molecular formula $C_{10}H_{16}$. The pinene family includes alpha-pinene, which may alternatively be referred to as pin-2(3)-ene, 2-pinene, or 2,6,6-trimethylbicyclo-[3.1.1]hept-2-ene. Alpha-pinene has the CAS numbers 2437-95-8 (±) and 80-56-8 (unspecified). The pinene family also includes beta-pinene, which may alternatively be referred to as pin-2(10)-ene, nopinene, pseudopinene or 6,6-dimethyl-2-methylenebicyclo-[3.1.1]heptane. Beta-pinene has the CAS numbers 23089-32-9 (±) and 127-91-3 (unspecified).

Other particularly preferred monoterpenes may include the phellandrenes. The phellandrenes belong to the monoterpene hydrocarbons. They have the molecular formula $C_{10}H_{16}$. They are colorless, oily liquids. They are a component of essential oils. The phellandrenes include (R)-α-phellandrene, which is alternatively known as (R)-2-methyl-5-(1-methylethyl)-1,3-cyclohexadiene and has the CAS number 4221-98-1. The phellandrene include (S)-α-phellandrene, which is alternatively known as (S)-2-methyl-5-(1-methylethyl)-1,3-cyclohexadiene and has Cas number 2243-33-6. The phellandrene include (R)-β-phellandrene, which is alternatively known as (R)-3-methylene-6-(1-methylethyl) cyclohexene and has the CAS number 6153-17-9. The phellandrene include (S)-β-phellandrene, which is alternatively known as (S)-3-methylene-6-(1-methylethyl)cyclohexene and has the CAS number 6153-16-8.

Menthone may also be used as another particularly preferred monoterpene. Menthone is a monocyclic monoterpene ketone with the molecular formula $C_{10}H_{18}O$. Menthone is also known alternatively as 2-propyl-(2)-5-methylcyclohexanone or as 2-isopropyl-5-methylcyclohexanone and has the CAS numbers 14073-97-3 ((2S,5R)-(−)-menthone, L-menthone) and 3391-87-5 ((2R,5S)-(+)-menthone D-menthone) and 89-80-5 (mixture of isomers).

Camphor may also be used as another particularly preferred monoterpene. Camphor is a bicyclic mono terpene ketone with the molecular formula $C_{10}H_{16}O$. Camphor may alternatively be referred to as camphor, as 1,7,7-trimethylbicyclo[2.2.1]heptan-2-one or as bornan-2-one and has the CAS numbers 76-22-2 [(±)-camphor], 464-49-3 [(+)-camphor] and 464-48-2 [(−)-camphor]. All stereoisomers of camphor are contemplated herein.

Camphene may also be used as another particularly preferred monoterpene. Camphene is a bicyclic monoterpene hydrocarbon, the molecular formula is $C_{10}H_{16}$. It occurs as a racemate of the two enantiomers, D- and L-camphene. Camphene may alternatively be referred to as 2,2-dimethyl-3-methylene-norbornane or 2,2-dimethyl-3-methylene-bicyclo[2.2.1]heptane and has CAS numbers 79-92-5 (enantiomeric mixture), 565-00-4 [(RS)-camphene], 5794-03-6 [(R)-camphene], and 5794-04-7 [(S)-camphene].

Borneols may also be used as other particularly preferred monoterpenes. Borneols are a naturally occurring group of secondary alcohols from the bicyclic monoterpene class of substances. Borneols include (+)-borneol, which is alternatively known as (1R,2S,4R)-1,7,7-trimethyl-bicyclo[2.2.1]heptan-2-ol and bears the CAS number 464-43-7. Borneols include (−)-borneol, which may alternatively be described as (1S,2R,4S)-1,7,7-trimethyl-bicyclo[2.2.1]heptan-2-ol and has the CAS number 464-45-9. Borneols also include (+)-isoborneol, which may alternatively be referred to as (1S, 2S,4S)-1,7,7-trimethyl-bicyclo[2.2.1]heptan-2-ol and has the CAS number 16725-71-6. Borneols also include (−)-isoborneol, which may alternatively be referred to as (1R, 2R,4R)-1,7,7-trimethyl-bicyclo[2.2.1]heptan-2-ol and has the CAS number 10334-13-1.

Fenchone may also be used as another preferred monoterpene. Fenchone is a bicyclic monoterpene ketone with the molecular formula $C_{10}H_{16}O$. It is found in fennel and is a component of many essential oils. Fenchone may alternatively be referred to as (+)-fenchone, (−)-fenchone, (±)-fenchone, (1S,4R)-1,3,3-trimethylbicyclo[2.2.1]heptan-2-one or as (1R,4S)-1,3,3-trimethylbicyclo[2.2.1]heptan-2-one. The CAS numbers of fenchone are 4695-62-9 [(+)-fenchone], 7787-20-4 [(−)-fenchone] and 1195-79-5 [(±)-Fenchone].

For example, farnesol may be used as a particularly preferred sesquiterpene. Farnesol is an acyclic sesquiterpene alcohol with a floral odor reminiscent of lily of the valley, which has the molecular formula $C_{15}H_{26}O$. Alternatively, farnesol may be referred to as 3,7,11-trimethyl-2,6,10-dodecatrien-1-ol or as (2E,6E)-3,7,11-trimethyl-2,6,10-dodecatrien-1-ol. Farnesol carries the CAS numbers 4602-84-0 (unspec.) and 106-28-5 (2E,6E).

Nerolidol may also be used as a particularly preferred sesquiterpene. Nerolidol belongs to the acyclic sesquiterpenes and has the molecular formula $C_{15}H_{26}O$. Alternatively, nerolidol may be referred to as 3,7,11-trimethyl-1,6,10-dodecatrien-3-ol. Nerolidol has the CAS number 7212-44-4 (mixture of isomers). All isomers of nerolidol are contemplated herein.

Bisabolol may also be used as a particularly preferred sesquiterpene. Bisabolol or (−)-α-bisabolol is a monocyclic sesquiterpene alcohol and has the molecular formula $C_{15}H_{26}O$. Alternatively, bisabolol may be referred to as (2S)-6-methyl-2-[(1S)-4-methylcyclohex-3-en-1-yl]hept-5-en-2-ol, or levomenol. Bisabolol has the CAS number 23089-26-1.

As a particularly preferred sesquiterpene, a compound from the group of curcumene may also be used. The curcumenes are a group of sesquiterpenes that can be isolated from the root of the ginger plant *Curcuma aromatica*, for example. They are widespread ingredients of numerous plants. A distinction is made between α-curcumene, both enantiomers [(R)-(−)-form, (S)-(+)-form] occur in nature}, β-curcumene and γ-curcumene.

Particularly good results have been obtained when the second composition (B) comprises one or more terpenes (B2) selected from the group of limonene, citronellol, geraniol, linalool, citral, citronellal, myrcene, carvone, alpha-terpinene, menthol, pinene, phellandrene, menthone, camphor, camphene, borneol, fenchone, farnesol, nerolidol, bisabolol and/or curcumene.

In a highly preferred version, a process as contemplated herein is exemplified in that the second composition (B) comprises one or more terpenes (B2) selected from the group of limonene, citronellol, geraniol, linalool, citral, citronellal, myrcene, carvone, alpha-terpinene, menthol, pinene, phellandrene, menthone, camphor, camphene, borneol, fenchone, farnesol, nerolidol, bisabolol and/or curcumene.

Limonene is the most preferred as a terpene (B2). In the context of an explicitly highly preferred version, a process as contemplated herein is therefore exemplified in that the second composition (B) comprises limonene (B2).

By selecting the appropriate amounts of terpenes (B2), the rate of film formation from the $C_1$-$C_6$ alkoxy silanes can be strongly influenced. For this reason, it has been found to be particularly preferable to use one or more terpenes (B2) in very specific ranges of amounts in the composition (B).

It is particularly preferred if the second composition (B) comprises—based on the total weight of the composition (B)—one or more terpenes (B2) in a total amount of from about 0.1 to about 20.0% by weight, preferably from about 0.2 to about 15.0% by weight, more preferably from about 0.5 to about 10.0% by weight, still more preferably from about 1.0 to about 8.0% by weight, and most preferably from about 2.0 to about 6.0% by weight.

In another particularly preferred version, a process as contemplated herein is exemplified in that the second composition (B) comprises—based on the total weight of the composition (B)—one or more terpenes (B2) in a total amount of from about 0.1 to about 20.0% by weight, preferably from about 0.2 to about 15.0% by weight, more preferably from about 0.5 to about 10.0% by weight, still more preferably from about 1.0 to about 8.0% by weight, and most preferably from about 2.0 to about 6.0% by weight The aforementioned terpenes are often used as ingredients in perfumes. During the work leading to the present disclosure, it has been found that perfumes, provided they contain at least one terpene (B2), also have a beneficial effect on condensation rates of $C_1$-$C_6$ alkoxysilanes. In this respect, this beneficial influence was observed in particular when the corresponding perfumes were used in the compositions (B) in such amounts that the terpenes (B2) were present in their preferred and particularly preferred ranges of amounts in the composition (B).

In a particularly preferred version, a method as contemplated herein is exemplified in that the second composition (B) comprises at least one perfume comprising one or more terpenes (B2).

Limonene is the most preferred terpene (B2), therefore perfumes containing limonene as a constituent or even more preferably as the main constituent are particularly preferred.

In a highly preferred version, a process as contemplated herein is exemplified in that the second composition (B) comprises at least one perfume containing limonene (B2).

A perfume which contains limonene as the main constituent is a perfume which -based on the total weight of the perfume—contains at least about 20.0% by weight, preferably at least about 30.0% by weight, more preferably at least about 40.0% by weight, still more preferably at least about 50.0% by weight and highly preferably at least about 60.0% by weight of limonene.

Fat Components in the Composition (B)

In addition to the terpenes (B2), the composition (B) may optionally comprise one or more further hydrophobic components or fatty components.

The fatty components are also hydrophobic substances which can form emulsions in the presence of water with the formation of micelle systems. In analogy to the terpenes, it is also assumed in this context that the $C_1$-$C_6$ alkoxysilanes—either in the form of their monomers or optionally in the form of their condensed oligomers—are embedded in this hydrophobic environment or in the micelle systems, so that the polarity of their environment changes. Due to the hydrophobic nature of the fatty components, the environment of the $C_1$-$C_6$ alkoxysilanes is also hydrophobized. It is assumed that the polymerization reaction of the $C_1$-$C_6$ alkoxy silanes leading to the film or coating takes place in an environment of reduced polarity at a reduced rate.

Particularly preferred, the fatty ingredients present in the composition (B) are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In a highly preferred version, a process as contemplated herein is exemplified in that the second composition (B) comprises at least one fat constituent from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In this context, highly preferred fat constituents are understood to be constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. For the purposes of the present disclosure, only non-ionic substances are explicitly considered as fat components. Charged compounds such as fatty acids and their salts are not considered as fat constituents.

The $C_{12}$-$C_{30}$ fatty alcohols may be saturated, mono- or polyunsaturated, linear or branched fatty alcohols with 12 to 30 C atoms.

Examples of preferred linear, saturated $C_{12}$-$C_{30}$ fatty alcohols include dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12, 15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol), and/or brassidyl alcohol ((13E)-docosen-1-ol).

The preferred representatives for branched fatty alcohols are 2-octyl-dodecanol, 2-hexyl-dodecanol and/or 2-butyl-dodecanol.

By selecting particularly well-suited fatty components, the polarity of the composition (B) can be optimally adjusted and the polymerization rate of the $C_1$-$C_6$ alkoxysilanes can be particularly well adapted to the respectively selected application conditions.

In this context, it has been found that in particular the use of at least one $C_{12}$-$C_{30}$ fatty alcohol in composition (B) creates an emulsion system in which the alkoxysilanes (A2) can be especially well embedded.

In one version, extremely good results were obtained when the second composition (B) comprises one or more $C_{12}$-$C_{30}$ fatty alcohols selected from the group of dodecan-1-ol (dodecyl alcohol, lauryl alcohol), Tetradecan-1-ol (tetradecyl alcohol, myristyl alcohol), Hexadecan-1-ol (hexadecyl alcohol, cetyl alcohol, palmityl alcohol), Octadecan-1-ol (Octadecyl alcohol, Stearyl alcohol), Arachyl alcohol (Eicosan-1-ol), Heneicosyl alcohol (Heneicosan-1-ol), Behenyl alcohol (docosan-1-ol), (9Z)-Octadec-9-en-1-ol (oleyl alcohol), (9E)-Octadec-9-en-1-ol (elaidyl alcohol), (9Z,12Z)-octadeca-9,12-dien-1-ol (linoleyl alcohol), (9Z, 12Z,15Z)-octadeca-9,12,15-trien-1-ol (linolenoyl alcohol), Gadoleyl alcohol ((9Z)-Eicos-9-en-1-ol), Arachidone alcohol ((5Z,8Z,11Z,14Z)-Eicosa-5,8,11,14-tetraen-1-ol), Erucyl alcohol ((13Z)-Docos-13-en-1-ol), brassidyl alcohol ((13E)-docosen-1-ol) 2-octyl-dodecanol, 2-hexyl-dodecanol and/or 2-butyl-dodecanol.

In an extremely preferred version, a process as contemplated herein is exemplified in that the second composition (B) comprises one or more $C_{12}$-$C_{30}$ fatty alcohols selected from the group of dodecan-1-ol (dodecyl alcohol, lauryl alcohol),
tetradecan-1-ol (tetradecyl alcohol, myristyl alcohol),
hexadecan-1-ol (hexadecyl alcohol, cetyl alcohol, palmityl alcohol),
octadecan-1-ol (octadecyl alcohol, stearyl alcohol),
arachyl alcohol (eicosan-1-ol),
heneicosyl alcohol (heneicosan-1-ol),
behenyl alcohol (docosan-1-ol),
(9Z)-Octadec-9-en-1-ol (oleyl alcohol),
(9E)-Octadec-9-en-1-ol (elaidyl alcohol),
(9Z,12Z)-octadeca-9,12-dien-1-ol (linoleyl alcohol),
(9Z,12Z,15Z)-octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-octyl-dodecanol,
2-hexyl dodecanol and/or
2-butyl-dodecanol.

By selecting the appropriate amounts of $C_{12}$-$C_{30}$ fatty alcohols, the rate of film formation from the $C_1$-$C_6$ alkoxy silanes can be strongly influenced. For this reason, it has been found to be highly preferable to use one or more $C_{12}$-$C_{30}$ fatty alcohols in very specific ranges of amounts.

It is particularly preferred if the second composition (B) comprises—based on the total weight of the composition (B)—one or more $C_{12}$-$C_{30}$ fatty alcohols (B) in a total amount of from about 2.0 to about 50.0% by weight, preferably from about 4.0 to about 40.0% by weight, more preferably from about 6.0 to about 30.0% by weight, still more preferably from about 8.0 to about 20.0% by weight, and most preferably from about 10.0 to about 15.0% by weight.

In another particularly preferred version, a process as contemplated herein is exemplified in that the second composition (B) comprises—based on the total weight of the composition (B)—one or more $C_{12}$-$C_{30}$ fatty alcohols (B) in a total amount of from about 2.0 to about 50.0% by weight, preferably from about 4.0 to about 40.0% by weight, more preferably from about 6.0 to about 30.0% by weight, still more preferably from about 8.0 to about 20.0% by weight, and most preferably from about 10.0 to about 15.0% by weight.

Furthermore, as a highly preferred fat ingredient, composition (B) may also comprise at least one $C_{12}$-$C_{30}$ fatty acid triglyceride which is $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the tri-ester of the trivalent alcohol glycerol with three equivalents of fatty acid. Both structurally identical and different fatty acids within a triglyceride molecule can be involved in ester formation.

As contemplated herein, fatty acids are understood to be saturated or unsaturated, unbranched or branched, unsubstituted or substituted $C_{12}$-$C_{30}$ carboxylic acids. Unsaturated fatty acids can be monounsaturated or polyunsaturated. In the case of an unsaturated fatty acid, its C—C double bond(s) may have the cis or trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11, 14-tetraenoic acid], and/or nervonic acid [(15Z)-tetracos-15-enoic acid].

The fatty acid triglycerides may also be of natural origin. The fatty acid triglycerides present in soybean oil, peanut oil, olive oil, sunflower oil, macadamia nut oil, moringa oil, apricot kernel oil, marula oil and/or optionally hydrogenated castor oil, or mixtures thereof, are particularly suitable for use in the product as contemplated herein.

A $C_{12}$-$C_{30}$ fatty acid monoglyceride is the monoester of the trihydric alcohol glycerol with one equivalent of fatty acid. In this case, either the central hydroxy group of the glycerol or the terminal hydroxy group of the glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z, 11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Here, either the middle and one terminal hydroxy group of glycerol may be esterified with two equivalents of fatty acid, or both terminal hydroxy groups of glycerol may be esterified with one fatty acid each. The glycerol can be esterified with two structurally identical or two different fatty acids.

Fatty acid diglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when composition (B) contained at least one $C_{12}$-$C_{30}$ fatty acid monoglyceride selected from the monoesters of glycerol with one equivalent of fatty acid selected from the group of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselic acid [(Z)-6-octadecenoic acid], Palmitoleic acid [(9Z)-Hexadec-9-enoic acid], Oleic acid [(9Z)-Octadec-9-enoic acid], Elaidic acid [(9E)-Octadec-9-enoic acid], Erucic acid [(13Z)-Docos-13-enoic acid], Linoleic acid [(9Z, 12Z)-Octadeca-9, 12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z, 8Z,11Z,14Z)-icosa-5,8,11,14-tetraenoic acid] and/or nervonic acid [(15Z)-tetracos-15-enoic acid].

In a particularly preferred version, a process as contemplated herein is exemplified in that the second composition (B) comprises at least one $C_{12}$-$C_{30}$ fatty acid monoglyceride selected from the monoesters of glycerol with one equivalent of fatty acid selected from the group of dodecanoic acid, tetradecanoic acid, hexadecanoic acid, tetracosanoic acid, octadecanoic acid, eicosanoic acid and/or docosanoic acid.

The choice of suitable amounts of $C_{12}$-$C_{30}$ fatty acid mono-, $C_{12}$-$C_{30}$ fatty acid di- and/or $C_{12}$-$C_{30}$ fatty acid triglycerides can also have a particularly strong influence on the rate of film formation from the $C_1$-$C_6$ alkoxy silanes. For this reason, it has been found to be particularly preferred to use one or more $C_{12}$-$C_{30}$ fatty acid mono-, $C_{12}$-$C_{30}$ fatty acid di- and/or $C_{12}$-$C_{30}$ fatty acid triglycerides in very specific amount ranges in composition (B).

With regard to the solution of the problem as contemplated herein, it proved to be highly preferable if the second composition (B) contained—based on the total weight of the composition (B)—one or more $C_{12}$-$C_{30}$ fatty acid mono-, $C_{12}$-$C_{30}$ fatty acid di- and/or $C_{12}$-$C_{30}$ fatty acid triglycerides in a total amount of from about 0.1 to about 20.0% by weight, preferably from about 0.3 to about 15.0% by weight, more preferably from about 0.5 to about 10.0% by weight and highly preferably from about 0.8 to about 5.0% by weight.

In a highly preferred version, a process as contemplated herein is exemplified in that the second composition (B) comprises—based on the total weight of the composition (B)—one or more $C_{12}$-$C_{30}$ fatty acid mono-, $C_{12}$-$C_{30}$ fatty acid di- and/or $C_{12}$-$C_{30}$ fatty acid triglycerides in a total amount of from about 0.1 to about 20.0% by weight, preferably from about 0.3 to about 15.0% by weight, more preferably from about 0.5 to about 10.0% by weight and highly preferably from about 0.8 to about 5.0% by weight.

The $C_{12}$-$C_{30}$ fatty acid mono-, $C_{12}$-$C_{30}$ fatty acid di- and/or $C_{12}$-$C_{30}$ fatty acid triglycerides may be used as sole fat components in the compositions (B). However, it is particularly preferred to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into composition (B).

Furthermore, as a highly preferred fatty ingredient, the composition (B) may also comprise at least one hydrocarbon.

Hydrocarbons are compounds formed exclusively of the atoms carbon and hydrogen with 8 to about 80 C-atoms. In this context, aliphatic hydrocarbons such as mineral oils, liquid paraffin oils (e.g. paraffinum liquidum or paraffinum perliquidum), isoparaffin oils, semisolid paraffin oils, paraffin waxes, hard paraffin (paraffinum solidum), petrolatum and polydecenes are particularly preferred.

Liquid paraffin oils (paraffinum liquidum and paraffinum perliquidum) have proved to be particularly suitable in this context. Especially preferred, the hydrocarbon is paraffinum liquidum, also known as white oil. Paraffinum Liquidum is a mixture of purified, saturated, aliphatic hydrocarbons, mainly including hydrocarbon chains with a C-chain distribution of about 25 to about 35 C-atoms.

Particularly good results were obtained when composition (B) contained at least one hydrocarbon selected from the group of mineral oils, liquid paraffin oils, isoparaffin oils, semisolid paraffin oils, paraffin waxes, hard paraffin (paraffinum solidum), petrolatum and polydecenes.

In a highly preferred version, a process as contemplated herein is exemplified in that the second composition (B) comprises at least one fatty constituent selected from the group of hydrocarbons.

The speed of film formation from the $C_1$-$C_6$ alkoxy silanes can also be particularly strongly influenced by the choice of suitable quantities of hydrocarbons. For this reason, it has been shown to be particularly preferred to use one or more hydrocarbons) in very specific ranges of amounts in the composition (B).

With regard to the solution of the problem as contemplated herein, it has proved to be particularly preferable if the second composition (B)—based on the total weight of the composition (B)—contained one or more hydrocarbons in a total amount of from about 0.5 to about 20.0% by weight, preferably from about 1.0 to about 15.0% by weight, more preferably from about 1.5 to about 10.0% by weight and extremely preferably from about 2.0 to about 8.0% by weight.

In a particularly preferred version, a process as contemplated herein is exemplified in that the second composition (B) comprises—based on the total weight of the composition (B)—one or more hydrocarbons in a total amount of from about 0.5 to about 20.0% by weight, preferably from about 1.0 to about 15.0% by weight, more preferably from about 1.5 to about 10.0% by weight and highly preferable from about 2.0 to about 8.0% by weight.

The hydrocarbon(s) may be used as the sole fatty ingredients in compositions (B). However, it is particularly preferred to incorporate at least one hydrocarbon in combination with at least one other constituent in the compositions (B).

It is particularly preferred if the composition (B) comprises at least one fatty constituent from the group of $C_{12}$-$C_{30}$ fatty alcohols and at least one other fatty constituent from the group of hydrocarbons.

Surfactants in the Composition (B)

Due to its content of water (B1) and terpene (B2), composition (B) is in the form of an emulsion or dispersion. In order to further optimize the formation of the emulsion/dispersion, it has been found to be particularly preferred to further use at least one surfactant in the composition (B).

It is particularly preferred if the composition (B) therefore additionally comprises at least one surfactant.

In another particularly preferred version, a process as contemplated herein is exemplified in that the second composition (B) comprises at least one surfactant.

The term surfactants (T) refers to surface-active substances that can form adsorption layers on surfaces and interfaces or aggregate in bulk phases to form micelle colloids or lyotropic mesophases. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

In a highly preferred version, a process as contemplated herein is exemplified in that the second composition (B) comprises at least one nonionic surfactant.

Non-ionic surfactants contain, for example, a polyol group, a polyalkylene glycol ether group or a combination of polyol and polyglycol ether group as a hydrophilic group. Such links include Addition products of about 2 to about 50 mol ethylene oxide and/or 0 to about 5 mol propylene oxide to linear and branched fatty alcohols with 6 to about 30 C atoms, the fatty alcohol polyglycol ethers or the fatty alcohol polypropylene glycol ethers or mixed fatty alcohol polyethers, Addition products of about 2 to about 50 moles of ethylene oxide and/or 0 to about 5 moles of propylene oxide to linear and branched fatty acids having 6 to about 30 carbon atoms, the fatty acid polyglycol ethers or the fatty acid polypropylene glycol ethers or mixed fatty acid polyethers, Addition products of about 2 to about 50 mol ethylene oxide and/or 0 to about 5 mol propylene oxide to linear and branched alkylphenols having 8 to about 15 C atoms in the alkyl group, the alkylphenol polyglycol ethers or the alkylpolypropylene glycol ethers or mixed alkylphenol polyethers, addition products of about 2 to about 50 moles of ethylene oxide and/or 0 to about 5 moles of propylene oxide to linear and branched fatty alcohols containing 8 to about 30 carbon atoms, to fatty acids containing 8 to about 30 carbon atoms and to alkylphenols containing 8 to about 15 carbon atoms in the alkyl group, terminated by a methyl or $C_2$-$C_6$ alkyl group, such as the grades obtainable under the sales names DEHYDOL® LS, DEHYDOL® LT (COGNIS™), $C_{12}$-$C_{30}$ fatty acid mono- and diesters of addition products of about 1 to about 30 moles of ethylene oxide to glycerol, addition products of about 5 to about 60 mol ethylene oxide to castor oil and hardened castor oil, polyol fatty acid esters, such as the commercial product HYDAGEN® HSP (COGNIS™) or SOVERMOL® types (COGNIS™), alkoxylated triglycerides, alkoxylated fatty acid alkyl esters of the formula (Tnio-1)

$$R_1CO\text{—}(OCH_2CHR2)_w OR_3 \quad \text{(Tnio-1)}$$

in which $R_1CO$ is a linear or branched, saturated and/or unsaturated acyl radical containing 6 to about 22 carbon atoms, $R_2$ is hydrogen or methyl, $R_3$ is a linear or branched alkyl radical containing 1 to 4 carbon atoms and w is a number of 1 to about 20, aminoxides, hydroxy mixed ethers, as described for example in DE-OS 19738866, sorbitan fatty acid esters and addition products of ethylene oxide to sorbitan fatty acid esters such as polysorbates, sugar fatty acid esters and addition products of ethylene oxide to sugar fatty acid ester, addition products of ethylene oxide to fatty acid alkanolamides and fatty amines, sugar tensides of the alkyl and alkenyl oligoglycoside type according to formula (E4-II),

$$R_4O\text{-}[G]_p \quad \text{(Tnio-2)}$$

where $R_4$ represents alkyl or alkenyl of 4 to 22 carbon atoms, G is a sugar radical of 5 or 6 carbon atoms and p represents numbers from 1 to about 10. They can be obtained by the relevant methods of preparative organic chemistry. The alkyl and alkenyl oligoglycosides can be derived from aldoses or ketoses with 5 or 6 carbon atoms, preferably glucose. The preferred alkyl and/or alkenyl oligoglycosides are thus alkyl and/or alkenyl oligoglucosides. The index number p in the general formula (Tnio-2) indicates the degree of oligomerization (DP), i.e. the distribution of mono- and oligoglycosides and stands for a number between 1 and about 10. While p must always be an integer in the individual molecule and can assume the values p=1 to 6, the value p for a certain alkyl oligoglycoside is an analytically determined arithmetical quantity, which usually represents a fractional number. Preferably, alkyl and/or alkenyl oligoglycosides with an average degree of oligomerization p of about 1.1 to about 3.0 are used. From an application technology point of view, those alkyl and/or alkenyl oligoglycosides are preferred whose degree of oligomerization is less than about 1.7 and in particular lies between about 1.2 and about 1.4. The alkyl or alkenyl radical $R_4$ can be derived from primary alcohols containing 4 to about 11, preferably 8 to about 10 carbon atoms. Typical examples are butanol, caproic alcohol, caprylic alcohol, caprin alcohol and undecrylic alcohol as well as their technical mixtures, such as those obtained in the hydrogenation of technical fatty acid methyl esters or in the course of the hydrogenation of aldehydes from Roelen's oxo synthesis. Preferred are alkyl oligoglucosides of chain length $C_8$-$C_{10}$ (DP=1 to 3), which are obtained as a precursor in the distillative separation of technical $C_8$-$C_{18}$ coconut fatty alcohol and may be contaminated with a proportion of less than about 6% by weight of C12 alcohol, and alkyl oligoglucosides based on technical C9/11 oxoalcohols (DP=1 to 3). Furthermore, the alkyl or alkenyl radical R15 can also be derived from primary alcohols having about 12 to about 22, preferably about 12 to about 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and their technical mixtures, which can be obtained as described above. Alkyl oligoglucosides based on hardened C12/14 coconut alcohol with a DP of 1 to 3 are preferred.

Sugar surfactants of the fatty acid N-alkyl polyhydroxyalkylamide type, a nonionic surfactant of formula (Tnio-3),

in which $R_5CO$ is an aliphatic acyl radical containing 6 to about 22 carbon atoms, $R_6$ is hydrogen, an alkyl or hydroxyalkyl radical containing 1 to 4 carbon atoms and [Z] is a linear or branched polyhydroxyalkyl radical containing 3 to about 12 carbon atoms and 3 to about 10 hydroxyl groups. The fatty acid N-alkyl polyhydroxyalkylamides are known substances which can usually be obtained by reductive amination of a reducing sugar with ammonia, an alkylamine or an alkanolamine and subsequent acylation with a fatty acid, a fatty acid alkyl ester or a fatty acid chloride. Preferably, the fatty acid N-alkyl polyhydroxyalkylamides are derived from reducing sugars having 5 or 6 carbon atoms, in particular from glucose. The preferred fatty acid N-alkyl polyhydroxyalkylamides are therefore fatty acid N-alkylglucamides as represented by the formula (Tnio-4):

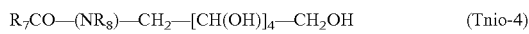

Preferably, glucamides of the formula (Tnio-4) are used as fatty acid-N-alkyl polyhydroxyalkylamides, in which $R_8$ represents hydrogen or an alkyl group and $R_7CO$ represents the acyl radical of caproic acid, caprylic acid, capric acid, Lauric acid, myristic acid, palmitic acid, palmitoleic acid, stearic acid, isostearic acid, oleic acid, elaidic acid, petroselinic acid, linoleic acid, linolenic acid, arachidic acid, gadoleic acid, behenic acid or erucic acid or their technical mixtures. Particularly preferred are fatty acid N-alkylglucamides of formula (Tnio-4) obtained by reductive amination of glucose with methylamine and subsequent acylation with lauric acid or C12/14 coconut fatty acid or a corresponding derivative. Furthermore, the polyhydroxyalkylamides can also be derived from maltose and palatinose.

The sugar surfactants may preferably be present in the compositions used as contemplated herein in amounts of about 0.1-20% by weight, based on the total composition. Amounts of about 0.5-15% by weight are preferred, and amounts of about 0.5-7.5% by weight are particularly preferred.

Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with about 2 to about 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R contains 6 to about 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. In this context, "normal" homolog distribution refers to mixtures of homologs obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly good results were obtained when a second composition (B) containing at least one ethoxylated fatty alcohol having a degree of ethoxylation of about 80 to about 120 was used in the process as contemplated herein.

In another highly preferred version, a process as contemplated herein is exemplified in that the second composition (B) comprises at least one nonionic surfactant of the formula (T-I),

wherein Ra represents a saturated or unsaturated, straight or branched $C_8$-$C_{24}$ alkyl group, preferably a saturated, straight C16 to C18 alkyl group, and n is an integer from about 80 to about 120, preferably an integer from about 90 to about 110 and particularly preferably the number 100.

A particularly suitable non-ionic surfactant of this type bears the trade name Brij S 100 or Brij S 100 PA SG. This is stearyl alcohol, ethoxylated with 100 EO, which is commercially available from Croda and has the CAS number 9005-00-9.

Furthermore, particularly good results were obtained when a second composition (B) containing at least one ethoxylated fatty alcohol having a degree of ethoxylation of 10 to 40 was used in the process as contemplated herein.

In another highly preferred version, a process as contemplated herein is exemplified in that the second composition (B) comprises at least one nonionic surfactant of the formula (T-II),

wherein

Rb represents a saturated or unsaturated, unbranched or branched $C_8$-$C_{24}$ alkyl group, preferably a saturated, unbranched C16 to C18 alkyl group, and m is an integer from about 10 to about 40, preferably an integer from about 20 to about 35 and particularly preferably the number 30.

A particularly well suited nonionic surfactant of this type is Ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin B3 from BASF®.

It has been found to be particularly preferred if the composition (B) comprises both at least one nonionic surfactant of formula (T-I) and at least one nonionic surfactant of formula (T-II).

Other Cosmetic Ingredients in the Composition (B)

In addition to the highly preferred ingredients already described above, the composition (B) may further comprise one or more additional cosmetic ingredients.

The cosmetic ingredients which may be optionally used in the composition (B) may be any suitable ingredients to impart further beneficial properties to the product. For example, the composition (A) may contain a solvent, a thickening or film-forming polymer, a surface-active compound from the group of nonionic, cationic, anionic or zwitterionic/amphoteric surfactants, coloring compounds from the group of pigments, direct dyes, oxidation dye precursors, fatty components from the group of $C_8$-$C_{30}$ fatty alcohols, hydrocarbon compounds, fatty acid esters, acids and bases belonging to the group of pH regulators, perfumes, preservatives, plant extracts and protein hydrolysates.

If the process as contemplated herein is a process for coloring keratinous material, the composition (B) may highly preferable comprise at least one coloring compound selected from the group of pigments and/or direct dyes.

The selection of these other substances will be made by the specialist according to the desired properties of the agents. With regard to other optional components and the quantities of these components used, explicit reference is made to the relevant manuals known to the specialist.

pH Values of the Compositions in the Process

In further experiments, it has been found that the pH values of compositions (A) and/or (B) can have an influence on the hydrolysis or condensation reactions described above which take place during use. It was found that alkaline pH values in particular stop condensation at the oligomer stage. The more acidic the reaction mixture, the stronger the condensation seems to proceed and the higher the molecular weight of the silane condensates formed during condensation. For this reason, it is preferred that compositions (A) and/or (B) have a pH of from about 7.0 to about 12.0, preferably from about 7.5 to about 11.5, more preferably from about 8.5 to about 11.0, and most preferably from about 9.0 to about 11.0.

The water content of composition (A) is at most about 10.0% by weight and is preferably set even lower. In some versions, the water content of the composition (B) may also be selected to be low. Especially in the case of compositions with a very low water content, the measurement of the pH value with the usual methods known from the prior art (pH value measurement by employing glass electrodes via combination electrodes or via pH indicator paper) can prove to be difficult. For this reason, the pH values as contemplated herein are those obtained after mixing or diluting the preparation in a weight ratio of about 1:1 with distilled water.

Accordingly, the corresponding pH is measured after, for example, 50 g of the composition has been mixed with 50 g of distilled water.

In another particularly preferred version, a process as contemplated herein, exemplified in that the composition (A) and/or (B), after dilution with distilled water in a weight ratio of about 1:1, has a pH of from about 7.0 to about 11.5, more preferably from about 8.5 to about 11.0 and most preferably from about 9.0 to about 11.0.

To adjust this alkaline pH, it may be necessary to add an alkalizing agent and/or acidifying agent to the reaction mixture. The pH values for the purposes of the present disclosure are pH values measured at a temperature of 22° C.

For example, ammonia, alkanolamines and/or basic amino acids can be used as alkalizing agents.

Alkanolamines may be selected from primary amines having a $C_2$-$C_6$ alkyl backbone bearing at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol.

For the purposes of the present disclosure, an amino acid is an organic compound containing in its structure at least one protonatable amino group and at least one —COOH or one —SO₃H group. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than 7.0.

Basic α-aminocarboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred version, an agent as contemplated herein is therefore exemplified in that the alkalizing agent is a basic amino acid from the group arginine, lysine, ornithine and/or histidine.

In addition, inorganic alkalizing agents can also be used. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Highly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In addition to the alkalizing agents described above, the specialist is familiar with common acidifying agents for fine adjustment of the pH value. As contemplated herein, preferred acidifiers are pleasure acids, such as citric acid, acetic acid, malic acid or tartaric acid, as well as diluted mineral acids.

Use of Compositions (A) and (B)

The method as contemplated herein comprises applying both compositions (A) and (B) to the keratinous material. It is essential to the process that compositions (A) and (B) come into contact with each other on the keratinous material. As previously described, this contact can be made either by mixing (A) and (B) beforehand or by successively applying (A) and (B) to the keratin material.

Work leading to the present disclosure has shown that composition (B) containing water (B1) and fatty components can have an optimum effect on the low-water silane blend (i.e. composition (A)), in particular when compositions (A) and (B) have been mixed together prior to use. This mixing can be done, for example, by stirring or shaking. It is particularly advantageous to prepare the two compositions (A) and (B) separately in two containers and then, before use, to transfer the entire quantity of composition (A) from its container into the container containing the second composition (B).

In a highly preferred version, a process as contemplated herein is exemplified in that a composition is applied to the keratinous material which has been prepared immediately before application by mixing the first composition (A) and the second composition (B).

The two compositions (A) and (B) may be mixed together in different proportions.

Especially preferred, composition (A) is used in the form of a relatively highly concentrated, low-water silane blend, which is quasi-diluted by mixing with composition (B). For this reason, it is particularly preferred to mix composition (A) with an excess by weight of composition (B). For example, 1 part by weight of (A) may be mixed with about 20 parts by weight of (B), or 1 part by weight of (A) may be mixed with about 10 parts by weight of (B), or 1 part by weight of (A) may be mixed with about 5 parts by weight of (B).

In a highly preferred version, a process as contemplated herein is exemplified in that a composition is applied to the keratinous material which has been prepared immediately before application by mixing the first composition (A) and the second composition (B) in a quantitative ratio (A)/(B) of from about 1:5 to about 1:20.

In principle, however, it is also possible to use composition (A) in excess by weight in relation to composition (B). For example, about 20 parts by weight of (A) may be mixed with 1 part by weight of (B), or about 10 parts by weight of (A) may be mixed with 1 part by weight of (B), or about 5 parts by weight of (A) may be mixed with 1 part by weight of (B).

Furthermore, it is also conceivable to apply the compositions (A) and (B) successively to the keratinous material, so that the contact of (A) and (B) only occurs on the keratinous material. In the context of this version, preferably no washing of the keratin matrix is carried out between the application of compositions (A) and (B), i.e., no treatment of the keratin matrix with water or water and surfactants.

In one version, only both compositions (A) and (B) may be used on the keratinous material. In particular, when using the method as contemplated herein for dyeing keratinous material, it may also be particularly preferred if not only the two compositions (A) and (B), but furthermore at least one third composition (C) is applied to the keratinous material.

In a process for coloring keratinous material, the third composition (C) may, for example, be a composition comprising at least one coloring compound selected from the group of pigments and/or direct dyes.

In the context of a further version, highly preferred is a process as contemplated herein in which the following is applied to the keratinous material
a third composition (C) comprising
at least one coloring compound selected from the group of pigments and/or direct dyes.

Using the three compositions (A), (B) and (C), various versions are as contemplated herein.

In one version, it is particularly preferred to prepare a mixture of the three compositions (A), (B) and (C) prior to application and then to apply this mixture to the keratin material.

In a particularly preferred version, a process as contemplated herein is exemplified in that a composition obtained immediately before use by mixing the first composition (A) with the second composition (B) and a third composition (C) is applied to the keratinous material, the third composition (C) comprising at least one coloring compound chosen from the group including comprising pigments and/or direct dyes.

When coloring the keratinous material, it may also be particularly preferred to prepare a mixture immediately before use by mixing the first composition (A) and the second composition (B) and to apply this mixture of (A) and (B) to the keratinous material. The third composition (C) containing the coloring compounds can then be added to the keratin material.

Within the framework of a highly preferred version, a process as contemplated herein is exemplified in that a composition is applied to the keratinous material, which was obtained immediately before the application by mixing the first composition (A) with the second composition (B), and subsequently the composition (C) is applied to the keratinous material.

In other words, a particularly preferred process as contemplated herein is exemplified in that, in a first step, a composition is applied to the keratinous material, which was prepared immediately before application by mixing the first composition (A) and the second composition (B), and, in a second step, the third composition (C) is applied to the keratinous material.

In addition to compositions (A) and (B)—or (A), (B) and (C)—a fourth composition (D) can also be applied to the keratin material as part of the process as contemplated herein. The application of the fourth composition (D) is particularly preferred in a dyeing process in order to reseal the previously obtained colorations. For this sealing, the composition (D) may contain, for example, at least one film-forming polymer.

In other words, further a highly preferred process as contemplated herein is one in which the following is applied to the keratinous material
a fourth composition (D) comprising
at least one film-forming polymer.

Coloring Compounds

When compositions (A) and (B)—or additionally optionally (C) and/or (D)—are used in a dyeing process, one or more coloring compounds may be employed.

In particular, the preparation (B) and/or the optional preparation (C) may additionally comprise at least one color-imparting compound.

The colorant compound or compounds may preferably be selected from pigments, direct dyes, oxidation dyes, photochromic dyes and thermochromic dyes, more preferably pigments and/or direct dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be visually assessed due to the high intensity of the pigment, which may be finely dispersed, the mixture is filtered. If a proportion of undissolved pigments remains on the filter paper, the solubility of the pigment is below 0.5 g/L.

Suitable color pigments can be of inorganic and/or organic origin.

In a preferred version, an agent as contemplated herein is exemplified in that it contains at least one coloring compound from the group of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. In particular, preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

Coloring compounds from the group of pigments which are also particularly preferred as contemplated herein are colored pearlescent pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

In a particularly preferred version, a process as contemplated herein is exemplified in that the composition (B) and/or the composition (C) comprise at least one coloring compound chosen from the group of inorganic pigments chosen from the group of colored metal oxides, metal hydroxides, metal oxide hydrates, silicates, metal sulfides, complex metal cyanides, metal sulphates, bronze pigments and/or colored mica- or mica-based pigments coated with at least one metal oxide and/or a metal oxychloride.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred version, the composition (B) and/or the composition (C) as contemplated herein is exemplified in that it comprises at least one coloring compound chosen from the group of pigments chosen from the group of colored metal oxides, metal hydroxides, metal oxide hydrates, silicates, metal sulfides, complex metal cyanides, metal sulphates, bronze pigments and/or from mica- or mica-based coloring compounds coated with at least one metal oxide and/or a metal oxychloride.

In a further preferred version, a composition (B) and/or composition (C) as contemplated herein is exemplified in that it comprises at least one coloring compound selected from mica- or mica-based pigments coated with one or more metal oxides selected from the group of titanium dioxide (CI 77891), black iron oxide (CI 77499), yellow iron oxide (CI 77492), red and/or brown iron oxide (CI 77491, CI 77499), manganese violet (CI 77742), ultramarines (sodium aluminum sulfo silicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names RONA®, COLORONA®, XIRONA®, DICHRONA® and TIMIRON® from MERCK®, ARIABEL® and UNI-PURE® from SENSIENT®, PRESTIGE® from ECKART® Cosmetic Colors and SUNSHINE® from Sunstar.

Particularly highly preferred color pigments with the trade name COLORONA® are, for example:

COLORONA® Copper, MERCK®, MICA, CI 77491 (IRON OXIDES)

COLORONA® Passion Orange, MERCK®, Mica, CI 77491 (Iron Oxides), Alumina

COLORONA® Patina Silver, MERCK®, MICA, CI 77499 (IRON OXIDES), CI 77891 (TITANIUM DIOXIDE)

COLORONA® RY, MERCK®, CI 77891 (TITANIUM DIOXIDE), MICA, CI 75470 (CARMINE)

COLORONA® Oriental Beige, MERCK®, MICA, CI 77891 (TITANIUM DIOXIDE), CI 77491 (IRON OXIDES)

COLORONA® Dark Blue, MERCK®, MICA, TITANIUM DIOXIDE, FERRIC FERROCYANIDE

COLORONA® Chameleon, MERCK®, CI 77491 (IRON OXIDES), MICA

COLORONA® Aborigine Amber, MERCK®, MICA, CI 77499 (IRON OXIDES), CI 77891 (TITANIUM DIOXIDE)

COLORONA® Blackstar Blue, MERCK®, CI 77499 (IRON OXIDES), MICA

COLORONA® Patagonian Purple, MERCK®, MICA, CI 77491 (IRON OXIDES), CI 77891 (TITANIUM DIOXIDE), CI 77510 (FERRIC FERROCYANIDE)

COLORONA® Red Brown, MERCK®, MICA, CI 77491 (IRON OXIDES), CI 77891 (TITANIUM DIOXIDE)

COLORONA® Russet, MERCK®, CI 77491 (TITANIUM DIOXIDE), MICA, CI 77891 (IRON OXIDES)

COLORONA® Imperial Red, MERCK®, MICA, TITANIUM DIOXIDE (CI 77891), D&C RED NO. 30 (CI 73360)

COLORONA® Majestic Green, MERCK®, CI 77891 (TITANIUM DIOXIDE), MICA, CI 77288 (CHROMIUM OXIDE GREENS)

COLORONA® Light Blue, MERCK®, MICA, TITANIUM DIOXIDE (CI 77891), FERRIC FERROCYANIDE (CI 77510)

COLORONA® Red Gold, MERCK®, MICA, CI 77891 (TITANIUM DIOXIDE), CI 77491 (IRON OXIDES)

COLORONA® Gold Plus MP 25, MERCK®, MICA, TITANIUM DIOXIDE (CI 77891), IRON OXIDES (CI 77491)

COLORONA® Carmine Red, MERCK®, MICA, TITANIUM DIOXIDE, CARMINE

COLORONA® Blackstar Green, MERCK®, MICA, CI 77499 (IRON OXIDES)

COLORONA® Bordeaux, MERCK®, MICA, CI 77491 (IRON OXIDES)

COLORONA® Bronze, MERCK®, MICA, CI 77491 (IRON OXIDES)

COLORONA® Bronze Fine, MERCK®, MICA, CI 77491 (IRON OXIDES)

COLORONA® Fine Gold MP 20, MERCK®, MICA, CI 77891 (TITANIUM DIOXIDE), CI 77491 (IRON OXIDES)

COLORONA® Sienna Fine, MERCK®, CI 77491 (IRON OXIDES), MICA

COLORONA® Sienna, MERCK®, MICA, CI 77491 (IRON OXIDES)

COLORONA® Precious Gold, MERCK®, Mica, CI 77891 (Titanium dioxide), Silica, CI 77491 (Iron oxides), Tin oxide COLORONA® Sun Gold Sparkle MP 29, MERCK®, MICA, TITANIUM DIOXIDE, IRON OXIDES, MICA, CI 77891, CI 77491 (EU)

COLORONA® Mica Black, MERCK®, CI 77499 (Iron oxides), Mica, CI 77891 (Titanium dioxide)

COLORONA® Bright Gold, MERCK®, Mica, CI 77891 (Titanium dioxide), CI 77491 (Iron oxides)

COLORONA® Blackstar Gold, MERCK®, MICA, CI 77499 (IRON OXIDES)

Other particularly preferred color pigments with the trade name XIRONA® are for example:

XIRONA® Golden Sky, MERCK®, Silica, CI 77891 (Titanium Dioxide), Tin Oxide

XIRONA® Caribbean Blue, MERCK®, Mica, CI 77891 (Titanium Dioxide), Silica, Tin Oxide XIRONA® Kiwi Rose, MERCK®, Silica, CI 77891 (Titanium Dioxide), Tin Oxide XIRONA® Magic Mauve, MERCK®, Silica, CI 77891 (Titanium Dioxide), Tin Oxide.

In addition, particularly preferred color pigments with the trade name UNIPURE® ® are for example:

UNIPURE® Red LC 381 EM, SENSIENT® CI 77491 (Iron Oxides), Silica

UNIPURE® Black LC 989 EM, SENSIENT®, CI 77499 (Iron Oxides), Silica

UNIPURE® Yellow LC 182 EM, SENSIENT®, CI 77492 (Iron Oxides), Silica

In a further version, the composition or preparation as contemplated herein' may also comprise one or more coloring compounds selected from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindigo, dioxazine and/or triarylmethane compounds.

Particularly suitable organic pigments are, for example, carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred version, a process as contemplated herein is exemplified in that the composition (B) and/or the composition (C) comprises at least one colorant compound from the group of organic pigments selected from the group of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

Furthermore, the organic pigment may also be a colored lacquer. as contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilicate, calcium aluminum borosilicate or even aluminum.

For example, alizarin color varnish can be used.

Due to their excellent resistance to light and temperature, the use of the aforementioned pigments is particularly preferred. It is also preferred if the pigments used have a certain particle size. This particle size leads on the one hand to an even distribution of the pigments in the formed polymer film and on the other hand avoids a rough hair or skin feeling after application of the cosmetic product. as contemplated herein, it is therefore advantageous if the at least one pigment has an average particle size $D_{50}$ of about 1.0 to about 50 μm, preferably about 5.0 to about 45 μm, preferably about 10 to about 40 μm, in particular about 14 to about 30 μm. The mean particle size $D_{50}$, for example, can be determined using dynamic light scattering (DLS).

The pigment or pigments may be used in an amount of from about 0.001 to about 20% by weight, in particular from about 0.05 to about 5% by weight, in each case based on the total weight of the composition or preparation as contemplated herein.

As colorant compounds, the compositions as contemplated herein may also comprise one or more direct dyes. Direct-acting dyes are dyes that draw directly onto the hair and do not require an oxidative process to form the color.

Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments. Preferably, the direct dyes in the sense of the present disclosure have a solubility in water (760 mmHg) at 25° C. of more than 1.0 g/L. More preferably, the direct dyes in the sense of the have a solubility in water (760 mmHg) at 25° C. of more than 1.5 g/L.

Direct dyes can be divided into anionic, cationic and non-ionic direct dyes.

In a further preferred version, an agent as contemplated herein is exemplified in that it comprises at least one anionic, cationic and/or nonionic direct dye as the coloring compound.

In a further preferred version, a process as contemplated herein is exemplified in that the composition (B) and/or the composition (C) comprises at least one colorant compound selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

Anionic direct dyes are also called acid dyes. Acid dyes are direct dyes which have at least one carboxylic acid grouping (—COOH) and/or one sulfonic acid grouping (—SO$_3$H). Depending on the pH, the protonated forms (—COOH, —SO$_3$H) of the carboxylic or sulfonic acid groups are in equilibrium with their deprotonated forms (—COO—, —SO$_3$— present). As the pH decreases, the proportion of protonated forms increases. If direct dyes are used in the form of their salts, the carboxylic acid groups or sulphonic acid groups are present in deprotonated form and are neutralized with corresponding stoichiometric equivalents of cations to maintain electro neutrality. Acid dyes as contemplated herein can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L. The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential feature of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

For example, one or more compounds from the following group may be selected as particularly suitable acid dyes: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF®), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Real Red D, FD&C Red Nr.2, Food Red 9, Naphthol Red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Acid Brilliant Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl)amino]phenyl}{4-[(N-ethyl(3-sulfonatobenzyl)imino]-2,5-cyclohexadien-1-ylidene}methyl)-benzenesulfonate and has a solubility in water of more than 20% by weight (25° C.).

Furthermore, thermochromic dyes can also be used. Thermochromism is the property of a material to change its color reversibly or irreversibly depending on the temperature. This can be done by changing the intensity and/or the wavelength maximum.

Finally, it is also possible to use photochromic dyes. Photochromism involves the property of a material to change its color reversibly or irreversibly depending on the irradiation with light, especially UV light. This can be done by changing the intensity and/or the wavelength maximum.

Film Forming Polymers

The preparations described above, in particular preparations (B), (C) and (D), highly preferred, preparation (D), may comprise at least one film-forming polymer.

Polymers are macromolecules with a molecular weight of at least about 1000 g/mol, preferably of at least about 2500 g/mol, particularly preferably of at least about 5000 g/mol, which include identical, repeating organic units. The polymers of the present disclosure may be synthetically produced polymers which are manufactured by polymerization of one type of monomer or by polymerization of different types of monomers which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. For the purposes of the present disclosure, it is preferred that the maximum molecular weight of the film-forming hydrophobic polymer (c) is not more than about 107 g/mol, preferably not more than about 106 g/mol and particularly preferably not more than about 105 g/mol.

As contemplated herein, a film-forming polymer is a polymer which is capable of forming a film on a substrate, for example on a keratinous material or a keratinous fiber. The formation of a film can be demonstrated, for example, by looking at the keratin material treated with the polymer under a microscope.

The film-forming polymers can be hydrophilic or hydrophobic.

In a first version, it may be preferred to use at least one hydrophobic film-forming polymer in preparation (B), (C) and/or (D), especially in preparation (D).

A hydrophobic polymer is defined as a polymer that has a solubility in water at 25° C. (760 mmHg) of less than 1% by weight.

The water solubility of the film-forming, hydrophobic polymer can be determined in the following way, for example. 1.0 g of the polymer is placed in a beaker. Make up to 100 g with water. A stir-fish is added and the mixture is heated to 25° C. on a magnetic stirrer while stirring. It is stirred for 60 minutes. The aqueous mixture is then visually assessed. If the polymer-water mixture cannot be assessed visually due to a high turbidity of the mixture, the mixture is filtered. If a proportion of undissolved polymer remains on the filter paper, the solubility of the polymer is less than 1% by weight.

These include acrylic acid-type polymers, polyurethanes, polyesters, polyamides, polyureas, cellulose polymers, nitrocellulose polymers, silicone polymers, acrylamide-type polymers and polyisoprenes.

Particularly well suited film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred version, a composition as contemplated herein is exemplified in that it comprises at least one film-forming, hydrophobic polymer (c) which is selected from the group of the copolymers of acrylic acid, the copolymers of methacrylic acid, the homopolymers or copolymers of acrylic acid esters, the homopolymers or copolymers of methacrylic acid esters homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming hydrophobic polymers selected from the group of synthetic polymers, polymers obtainable by free-radical polymerization or natural polymers have proved to be particularly suitable for solving the problem as contemplated herein.

Other particularly well-suited film-forming hydrophobic polymers may be selected from the homopolymers or copolymers of olefins, such as cycloolefins, butadiene, isoprene or styrene, vinyl ethers, vinyl amides, the esters or amides of (meth)acrylic acid having at least one $C_1$-$C_{20}$ alkyl group, an aryl group or a $C_2$-$C_{10}$ hydroxyalkyl group.

Further film forming hydrophobic polymers may be selected from the homo- or copolymers of isooctyl (meth)acrylate; isononyl (meth)acrylate; 2-ethylhexyl (meth)acrylate; lauryl (meth)acrylate); isopentyl (meth)acrylate; n-butyl (meth)acrylate); isobutyl (meth)acrylate; ethyl (meth)acrylate; methyl (meth)acrylate; tert-butyl (meth) acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming hydrophobic polymers may be selected from the homo- or copolymers of (meth)acrylamide; N-alkyl-(meth)acrylamides, in particular those containing $C_2$-$C_{18}$ alkyl groups, such as N-ethyl-acrylamide, N-tert-butyl-acrylamide, le N-octyl-acrylamide; N-di($C_1$-$C_4$)alkyl-(meth)acrylamide.

Other preferred anionic copolymers are, for example, copolymers of acrylic acid, methacrylic acid or their $C_1$-$C_6$ alkyl esters, as sold under the INCI declaration Acrylates Copolymers. A suitable commercial product is, for example, ACULYN® 33 from Rohm & Haas. However, copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, ACULYN®22 (Acrylates/Steareth-20 Methacrylate Copolymer), ACULY® 28 (Acrylates/Beheneth-25 Methacrylate Copolymer), STRUCTURE® 2001 (Acrylates/Steareth-20 Itaconate Copolymer), STRUCTURE® 3001 (Acrylates/Ceteth-20 Itaconate Copolymer), STRUCTURE® Plus (Acrylates/Aminoacrylates C10-30 Alkyl PEG-20 Itaconate Copolymer), CARBOPOL® 1342, 1382, Ultrez 20, Ultrez 21 (Acrylates/C10-30 Alkyl Acrylate Crosspolymer), SYNTHALEN® W 2000 (Acrylates/Palmeth-25 Acrylate Copolymer) or Soltex OPT (Acrylates/C12-22 Alkyl methacrylate Copolymer) distributed by Rohme und Haas.

Suitable polymers based on vinyl monomers may include, for example, the homopolymers and copolymers of N-vinylpyrrolidone, vinylcaprolactam, vinyl-($C_1$-$C_6$)alkyl-pyrrole, vinyl-oxazole, vinyl-thiazole, vinylpyrimidine, vinylimidazole.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable polymers based on olefins may include, for example, the homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF® under the trade name "Luvitol HSB".

It was also possible to obtain intense and washfast staining when the preparation (B), (C) and/or (D), particularly in the preparation (D), contained at least one film-forming polymer selected from the group of the homopolymers and copolymers of acrylic acid, the homopolymers and copolymers of methacrylic acid, the homopolymers and copolymers of acrylic acid esters, the homopolymers and copolymers of methacrylic acid esters, the homopolymers and copolymers of acrylic acid amides homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred version, a method as contemplated herein is exemplified in that the preparation (B), (C) and/or (D), most particularly the preparation (D), contains at least one film-forming polymer selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a first version, it may be preferred to use at least one hydrophilic film-forming polymer in preparation (B), (C) and/or (D), especially in preparation (D).

A hydrophilic polymer is defined as a polymer having a solubility in water at 25° C. (760 mmHg) of more than 1% by weight, preferably more than 2% by weight.

The water solubility of the film-forming, hydrophilic polymer can be determined in the following way, for example. 1.0 g of the polymer is placed in a beaker. Make up to 100 g with water. A stir-fish is added and the mixture is heated to 25° C. on a magnetic stirrer while stirring. It is stirred for 60 minutes. The aqueous mixture is then visually assessed. A completely dissolved polymer appears macroscopically homogeneous. If the polymer-water mixture cannot be assessed visually due to a high turbidity of the mixture, the mixture is filtered. If no undissolved polymer remains on the filter paper, the solubility of the polymer is more than 1% by weight.

Nonionic, anionic and cationic polymers can be used as film-forming, hydrophilic polymers.

Suitable film-forming hydrophilic polymers can be selected, for example, from the group of polyvinylpyrrolidone (co)polymers, polyvinyl alcohol (co)polymers, vinyl acetate (co)polymers, carboxyvinyl(co)polymers, acrylic acid (co)polymers, methacrylic acid (co)polymers, natural gums, polysaccharides and/or acrylamide (co)polymers.

Furthermore, it is particularly preferred to use polyvinylpyrrolidone (PVP) and/or a vinylpyrrolidone-containing copolymer as the film-forming hydrophilic polymer.

In another particularly preferred version, an agent as contemplated herein is exemplified in that it contains (c) at least one film-forming, hydrophilic polymer selected from the group of polyvinylpyrrolidone (PVP) and the copolymers of polyvinylpyrrolidone.

It is further preferred if the agent as contemplated herein comprises polyvinylpyrrolidone (PVP) as the film-forming hydrophilic polymer. Surprisingly, the wash fastness of the colorations obtained with agents containing PVP (b9 was also very good.

Particularly well suited polyvinylpyrrolidones are, for example, available under the name LUVISKOL® K from BASF® SE, especially LUVISKOL® K 90 or LUVISKOL® K 85 from BASF® SE.

The polymer PVP K30, which is marketed by ASHLAND® (ISP, POI Chemical), can also be used as another explicitly very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115 and available from BASF®.

The use of film-forming hydrophilic polymers from the group of copolymers of polyvinylpyrrolidone has also led to particularly good and washfast color results.

Vinylpyrrolidone-vinyl ester copolymers, such as those marketed under the trademark LUVISKOL® (BASF®), are particularly suitable film-forming hydrophilic polymers. LUVISKOL® VA 64 and LUVISKOL® VA 73, both vinylpyrrolidone/vinyl acetate copolymers, are particularly preferred non-ionic polymers.

Of the vinylpyrrolidone-containing copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed by BASF® SE under the name LUVISKOL® VA. For example, a VPNinyl Caprolactam/DMAPA Acrylates copolymer is sold under the trade name AQUAFLEX® SF-40 by ASHLAND® Inc. For example, a VP/DMAPA acrylates copolymer is marketed by ASHLAND® under the name STYLEZE® CC-10 and is a highly preferred vinylpyrrolidone-containing copolymer.

Other suitable copolymers of polyvinylpyrrolidone may also be those obtained by reacting N-vinylpyrrolidone with at least one further monomer from the group of V-vinylformamide, vinyl acetate, ethylene, propylene, acrylamide, vinylcaprolactam, vinylcaprolactone and/or vinyl alcohol.

In another particularly preferred version, an agent as contemplated herein is exemplified in that it comprises at least one film-forming hydrophilic polymer selected from the group of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another useful copolymer of vinylpyrrolidone is the polymer known by the INCI name maltodextrin/VP copolymer.

Furthermore, intensively dyed keratin material, especially hair, with very good washfastness could be obtained if a non-ionic, film-forming, hydrophilic polymer was used as the film-forming, hydrophilic polymer.

In a first version, it may be preferred if preparation (B), (C) and/or (D), in particular preparation (D), comprise at least one non-ionic, film-forming, hydrophilic polymer.

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include, for example, quaternized ammonium groups but not protonated amines. Anionic groups include carboxylic and sulphonic acid groups.

Particular preference is given to products containing, as a non-ionic, film-forming, hydrophilic polymer, at least one polymer selected from the group of Polyvinylpyrrolidone,
Copolymers of N-vinylpyrrolidone and vinyl esters of carboxylic acids having 2 to 18 carbon atoms, in particular of N-vinylpyrrolidone and vinyl acetate,
Copolymers of N-vinylpyrrolidone and N-vinylimidazole and methacrylamide,
Copolymers of N-vinylpyrrolidone and N-vinylimidazole and acrylamide,
Copolymers of N-vinylpyrrolidone with N,N-di(C1 to C4)-alkylamino-(C2 to C4)-alkylacrylamide, If copolymers of N-vinylpyrrolidone and vinyl acetate are used, it is again preferable if the molar ratio of the structural units contained in the monomer N-vinylpyrrolidone to the structural units of the polymer contained in the monomer vinyl acetate is in the range from about 20:80 to about 80:20, in particular from about 30:70 to about 60:40. Suitable copolymers of vinylpyrrolidone and vinyl acetate are available, for example, under the trademarks LUVISKOL® VA 37, LUVISKOL® VA 55, LUVISKOL® VA 64 and LUVISKOL® VA 73 from BASF® SE.

Another particularly preferred polymer is selected from the INCI designation VP/Methacrylamide/Vinyl Imidazole Copolymer, which is available under the trade name LUVISET® Clear from BASF® SE.

Another particularly preferred non-ionic, film-forming, hydrophilic polymer is a copolymer of N-vinylpyrrolidone and N,N-dimethylaminiopropylmethacrylamide, which is sold under the INCI designation VP/DMAPA Acrylates Copolymer e.g. under the trade name STYLEZE® CC 10 by ISP.

A cationic polymer as contemplated herein is the copolymer of N-vinylpyrrolidone, N-vinylcaprolactam, N-(3-dimethylaminopropyl)methacrylamide and 3-(methacryloylamino)propyl-lauryl-dimethylammonium chloride (INCI designation: polyquaternium-69), which is marketed, for example, under the trade name AQUASTYLE®300 (28-32% by weight of active substance in ethanol-water mixture, molecular weight 350000) by ISP.

Other suitable film-forming, hydrophilic polymers include

Vinylpyrrolidone-vinylimidazolium methochloride copolymers, as offered under the designations LUVIQUAT® FC 370, FC 550 and the INCI designation Polyquaternium-16 as well as FC 905 and HM 552,
Vinylpyrrolidone-vinylcaprolactam-acrylate terpolymers, as they are commercially available with acrylic acid esters and acrylic acid amides as a third monomer component, for example under the name AQUAFLEX® SF 40.

Polyquaternium-11 is the reaction product of diethyl sulphate with a copolymer of vinyl pyrrolidone and dimethylaminoethyl methacrylate. Suitable commercial products are available under the names DEHYQUART® CC 11 and LUVIQUAT® PQ 11 PN from BASF® SE or GAFQUAT® 440, GAFQUAT® 734, GAFQUAT® 755 or GAFQUAT® 755N from ASHLAND® Inc.

Polyquaternium-46 is the reaction product of vinylcaprolactam and vinylpyrrolidone with methylvinylimidazolium methosulfate and is available for example under the name LUVIQUAT® Hold from BASF® SE. Polyquaternium-46 is preferably used in an amount of about 1 to about 5% by weight—based on the total weight of the cosmetic composition. It particularly prefers to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names CARBOPOL® 980, 981, 954, 2984 and 5984 by Lubrizol or under the names SYNTHALEN® M and SYNTHALEN® K by 3V Sigma (The Sun Chemicals, Inter Harz).

Examples of suitable film-forming hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers which are produced from monomers of (methyl)acrylamido-$C_1$-$C_4$-alkyl sulphonic acid or the salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of poly(meth)acrylamido-$C_1$-$C_4$-alkyl sulfonic acids are crosslinked and at least about 90% neutralized. These polymers can or cannot be cross-linked.

Cross-linked and totally or partially neutralized polymers of the poly-2-acrylamido-2-methylpropane sulphonic acid type are known under the INCI designation "Ammonium Polyacrylamido-2-methylpropanesulphonates" or "Ammonium Polyacryldimethyltauramides".

Another preferred polymer of this type is the cross-linked poly-2-acrylamido-2-methyl-propanesulphonic acid polymer marketed by Clamant under the trade name Hostacerin AMPS, which is partially neutralized with ammonia.

In a further explicitly highly preferred version, a process as contemplated herein is exemplified in that the preparation (B), (C) and/or (D), particularly the preparation (D), comprises at least one anionic, film-forming, polymer.

In this context, the best results were obtained when preparation (B), (C) and/or (D), and more particularly preparation (D), contains at least one film-forming polymer comprising at least one structural unit of formula (P-I) and at least one structural unit of formula (P-II).

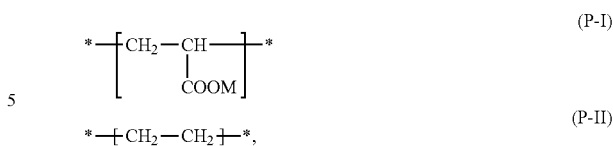

where
M represents a hydrogen atom or ammonium ($NH_4$), sodium, potassium, ½ magnesium or ½ calcium.

In a further preferred version, a method as contemplated herein is exemplified in that the preparation (B), (C) and/or (D), most particularly the preparation (D), includes at least one film-forming polymer comprising at least one structural unit of the formula (P-I) and at least one structural unit of the formula (P-II)

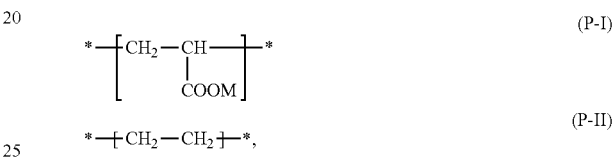

where
M represents a hydrogen atom or ammonium ($NH_4$), sodium, potassium, %2 magnesium or %2 calcium.

When M represents a hydrogen atom, the structural unit of the formula (P-I) is based on an acrylic acid unit.

When M is an ammonium counterion, the structural unit of the formula (P-I) is based on the ammonium salt of acrylic acid.

When M represents a sodium counterion, the structural unit of the formula (P-I) is based on the sodium salt of acrylic acid.

When M represents a potassium counterion, the structural unit of the formula (P-I) is based on the potassium salt of acrylic acid.

When M is a half equivalent of a magnesium counterion, the structural unit of the formula (P-I) is based on the magnesium salt of acrylic acid.

When M represents half an equivalent of a calcium counterion, the structural unit of the formula (P-I) is based on the calcium salt of acrylic acid.

The film-forming polymer(s) as contemplated herein is/are preferably used in certain ranges of amounts in the preparations (B), (C) and/or (D). In this context, it has been shown to be particularly preferred for solving the problem as contemplated herein if the preparation contains—in each case based on its total weight—one or more film-forming polymers in a total amount of from about 0.1 to about 18.0% by weight, preferably from about 1.0 to about 16.0% by weight, more preferably from about 5.0 to about 14.5% by weight and highly preferably from about 8.0 to about 12.0% by weight.

In a further preferred version, a process as contemplated herein is exemplified in that the preparation (B), (C) and/or (D) contains—based on their respective total weight—one or more film-forming polymers in a total amount of from about 0.1 to about 18.0% by weight, preferably from about 1.0 to about 16.0% by weight, more preferably from about 5.0 to about 14.5% by weight and highly preferably from about 8.0 to about 12.0% by weight.

Multi-Component Packaging Unit (Kit-of-Parts)

To increase user convenience, all preparations necessary for the application process, in particular for the dyeing process, are provided to the user in the form of a multi-component packaging unit (kit-of-parts).

A second subject of the present disclosure is therefore a multi-component packaging unit (kit-of-parts) for treating keratinous material, comprehensively packaged separately from one another.
- a first container comprising a first composition (A) and
- a second container comprising a second composition (B), wherein compositions (A) and (B) having already been disclosed in detail in the description of the first subject matter of the present disclosure.

Furthermore, the multi-component packaging unit as contemplated herein may further comprise a third packaging unit containing a cosmetic preparation (C). The preparation (C) contains, as described above, particularly preferably at least one color-imparting compound.

In a highly preferred version, the multi-component packaging unit (kit-of-parts) as contemplated herein comprises separately assembled
- a third container comprising a third composition (C), the third composition (C) having already been disclosed in detail in the description of the first subject matter of the present disclosure.

Furthermore, the multi-component packaging unit as contemplated herein may further comprise a fourth packaging unit containing a cosmetic preparation (D). The preparation (D) contains, as described above, particularly preferably at least one film-forming polymer.

In a highly preferred version, the multi-component packaging unit (kit-of-parts) as contemplated herein comprises separately assembled
- a fourth container comprising a fourth composition (D), the fourth composition (D) having already been disclosed in detail in the description of the first subject matter of the present disclosure.

With respect to the other preferred versions of the multi-component packaging unit as contemplated herein, the same applies mutatis mutandis to the procedure as contemplated herein.

EXAMPLES

1 Preparation of the Silane Blend (Composition (A))

A reactor with heatable/coolable outer shell and with a capacity of 10 liters was filled with 4.67 kg of methyltrimethoxysilane (34.283 mol). With stirring, 1.33 kg of (3-aminopropyl)triethoxysilane (6.008 mol) was then added. This mixture was stirred at 30° C. Subsequently, 670 ml of distilled water (37.18 mol) was added dropwise with vigorous stirring while maintaining the temperature of the reaction mixture at 30° C. under external cooling. After completion of the water addition, stirring was continued for another 10 minutes. A vacuum of 280 mbar was then applied and the reaction mixture heated to a temperature of 44° C. Once the reaction mixture reached the temperature of 44° C., the ethanol and methanol released during the reaction were distilled off over a period of 190 minutes. In the course of distillation, the vacuum was lowered to 200 mbar. The distilled alcohols were collected in a cooled receiver. The reaction mixture was then allowed to cool to room temperature. To the mixture thus obtained, 3.33 kg of hexamethyldisiloxane was then dropped with stirring. It was stirred for 10 minutes. In each case, 100 ml of the silane blend was filled into a bottle with a capacity of 100 ml and screw cap with seal. After filling, the bottles were tightly sealed. The water content was less than 2.0% by weight.

2 Preparation of the Composition (B)

The following compositions (B) were prepared (unless otherwise stated, all figures are in % by weight).

| Composition (B) | | |
|---|---|---|
| | B-V1<br>Gel<br>Comparison | B-E1<br>Emulsion<br>Present<br>disclosure |
| Hydroxyethyl cellulose | 1.0 | 1.0 |
| Limonene | — | 5.0 |
| Ceteareth-30 (Cetearyl alcohol, ethoxylated with 30 EO) | — | 2.4 |
| Brij S 100 PA SG (stearyl alcohol, ethoxyl value with 100 EO, Croda) | — | 1.2 |
| Water (distilled) | ad 100 | ad 100 |

3 Preparation of Compositions (C) and (D)

The following compositions were prepared (unless otherwise stated, all figures are in % by weight).

| Composition (C) | |
|---|---|
| | % in weight |
| Lavanya Belmont Phthalocyanine blue pigment CI 74160 | 35.0 |
| PEG-12 Dimethicone | ad 100 |

| Composition (D) | |
|---|---|
| | % in weight |
| Ethylene/Sodium Acrylate Copolymer (25% solution) | 40.0 |
| Water | ad 100 |

5 Application

The ready-to-use composition was prepared by mixing 1.5 g of the composition (A), 20.0 g of the composition (B) and 1.5 g of the composition (C), respectively. Compositions (A), (B) and (C) were shaken for 1 minute each. Then this ready-to-use agent was dyed on two strands of hair (Kerling, Euronatural hair white) each.

Three minutes after completion of shaking, the ready-to-use composition was applied to a first strand (strand 1), left to act for 1 min, and then rinsed out. 10 min after completion of shaking, the ready-to-use composition was applied to a second strand (strand 2), left to act for 1 min, and then rinsed out.

Subsequently, the composition (D) was applied to each strand of hair, left to act for 1 minute and then also rinsed with water.

The two dyed strands were each dried and visually compared under a daylight lamp.

| | | |
|---|---|---|
| Step one: | (A) + (B – V1) + (C) | (A) + (B – E1) + (C) |
| Step two: | D | D |
| Color difference between strand 1 and 2 | high | low |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment. It being understood that various changes may be made in the function and arrangement of elements described in an exemplary embodiment without departing from the scope of the various embodiments as set forth in the appended claims.

The invention claimed is:

1. A method for treating keratinous material, comprising:
applying a first composition (A) to the keratinous material, wherein the first composition (A) comprises,
(A1) less than 10% by weight of water, relative to a total weight of the composition (A), and
(A2) one or more organic C1-C6 alkoxy silanes and/or their condensation products, and
applying a second composition (B) to the keratinous material, wherein the second composition (B) comprises
(B1) water and
(B2) one or more terpenes, wherein the one or more terpenes are present in the second composition in an amount of from about 5 to about 8 weight percent, based on a total weight of the second composition.

2. The method according to claim 1, wherein:
the first composition (A) comprises the one or more organic $C_1$-$C_6$ alkoxy silanes (A2), wherein the one or more organic $C_1$-$C_6$ alkoxy silanes are of formula (S-I) and/or (S-II),

   (S-I)

where
$R_1$, $R_2$ independently represent a hydrogen atom or a $C_1$-$C_6$ alkyl group,
L is a linear or branched divalent $C_1$-$C_{20}$ alkylene group,
$R_3$, $R_4$ independently represent a $C_1$-$C_6$ alkyl group,
a, stands for an integer from 1 to 3, and
b is the integer 3-a, and

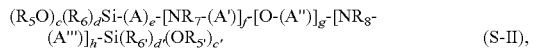   (S-II), where
$R_5$', $R_5$'', $R_6$, $R_6$' and $R_6$'' independently represent a $C_1$-$C_6$ alkyl group,
A, A', A'', A''' and A'''' independently represent a linear or branched $C_1$-$C_{20}$ divalent alkylene group,
$R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of the formula (S-III),

   (S-III), wherein
c stands for an integer from 1 to 3,
d stands for the integer 3-c,
c' c' stands for an integer from 1 to 3,
d' stands for the integer 3-c',
c'' stands for an integer from 1 to 3,
d'' stands for the integer 3-c'',
e stands for 0 or 1,
f stands for 0 or 1,
g stands for 0 or 1,
h stands for 0 or 1,
provided that at least one of e, f, g and h is different from 0,
and/or their condensation products.

3. The method according to claim 2, wherein the first composition (A) comprises the at least one $C_1$-$C_6$ organic alkoxysilane (A2) of formula (S-I) chosen from the group of
(3-aminopropyl)triethoxysilane,
(3-aminopropyl)trimethoxysilane,
(2-aminoethyl)triethoxysilane,
(2-aminoethyl)trimethoxysilane,
(3-dimethylaminopropyl)triethoxysilane,
(3-dimethylaminopropyl)trimethoxysilane,
(2-dimethylaminoethyl)triethoxysilane,
(2-dimethylaminoethyl)trimethoxysilane,
combinations thereof,
and/or and their condensation products.

4. The method according to claim 2, wherein the first composition (A) comprises the one or more organic $C_1$-$C_6$ alkoxy silanes (A2), and wherein the one or more organic $C_1$-$C_6$ alkoxy silanes (A2) further comprise a compound of formula (S-IV),

   (S-I), where
$R_9$ represents a $C_1$-$C_{12}$ alkyl group,
$R_{10}$ stands for a $C_1$-$C_6$ alkyl group,
$R_{11}$ stands for a $C_1$-$C_6$ alkyl group
k is an integer from 1 to 3, and
m stands for the integer 3-k,
and/or their condensation products.

5. The method according to claim 4, wherein the first composition (A) comprises the at least one $C_1$-$C_6$ organic alkoxy silane (A2) of formula (S-IV) chosen from the group of methyltrimethoxysilane, methyltriethoxysilane, ethyltrimethoxysilane, ethyltriethoxysilane, hexyltrimethoxysilane, hexyltriethoxysilane, octyltrimethoxysilane, octyltriethoxysilane, dodecyltrimethoxysilane, dodecyltriethoxysilane, combinations thereof, and their condensation products.

6. The method according to claim 1, wherein the first composition (A) further comprises at least one cosmetic ingredient from the group of hexamethyldisiloxane, octamethyltrisiloxane, decamethyltetrasiloxane, hexamethylcyclotrisiloxane, octamethylcyclotetrasiloxane and decamethylcyclopentasiloxane.

7. The method according to claim 1, wherein the first composition (A) comprises about 10.0 to about 50.0% by weight of hexamethyldisiloxane, based on the total weight of the composition (A).

8. The method according to claim 1, wherein the second composition (B) comprises the one or more terpenes (B2) selected from the group of monoterpenes having 10 carbon atoms, sesquiterpenes having 15 carbon atoms, and diterpenes having 20 carbon atoms.

9. The method according to claim 1, wherein the second composition (B) comprises the one or more terpenes (B2) selected from the group of limonene, citronellol, geraniol, linalool, citral, citronellal, myrcene, carvone, alpha-terpinene, menthol, pinene, phellandrene, menthone, camphor, camphene, borneol, fenchone, farnesol, nerolidol, bisabolol and curcumene.

10. The method according to claim 1, wherein the second composition (B) comprises limonene.

11. The method according to claim 1, wherein the second composition (B) comprises at least one fat constituent selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and hydrocarbons.

12. The method according to claim 11, wherein the second composition (B) comprises one or more of the $C_{12}$-$C_{30}$ fatty alcohols from the group of Dodecan-1-ol, Tetradecan-1-ol, Hexadecan-1-ol, Octadecan-1-ol, Eicosan-1-ol, Heneicosan-1-ol, Docosan-1-ol, (9Z)-Octadec-9-en-1-ol, (9E)-Octadec-9-en-1-ol, (9Z,12Z)-Octadeca-9,12-dien-1-ol, (9Z,12Z, 15Z)-Octadeca-9,12, 15-trien-1-ol, (9Z)-Eicos-9-en-1-ol, (5Z,8Z,11Z,14Z)-Eicosa-5,8,11,14-tetraen-1-ol, (13Z)-Docos-13-en-1-ol), (13E)-Docosen-1-ol), 2-Octyl-dodecanol, 2-Hexyl-Dodecanol and 2-Butyl-dodecanol.

13. The method according to claim 1, wherein a composition is applied to the keratinous material, the composition was prepared before application by mixing the first composition (A) and the second composition (B).

14. The method according to claim 1, further comprising:
applying a third composition (C) to the keratinous material, wherein the third composition (C) comprises at least one coloring compound selected from the group of pigments and direct dyes.

15. The method according to claim 14, further comprising:
mixing the first composition (A) with the second composition (B) and the third composition (C); and
applying the mixture of the first composition (A), the second composition (B), and the third composition (C) to the keratinous material.

16. The method according to claim 1, further comprising:
applying a fourth composition (D) to the keratinouos material, wherein the fourth composition comprises;
at least one film-forming polymer.

17. The method according to claim 14, wherein one or more of the composition (B) and the composition (C) comprise at least one coloring compound chosen from the group of colored metal oxides, metal hydroxides, metal oxide hydrates, silicates, metal sulfides, complex metal cyanides, metal sulphates, bronze pigments, colored mica- or mica-based pigments coated with at least one metal oxide, a metal oxychloride, and combinations thereof.

18. A kit-of-parts for treating keratinous material, comprising separately packaged
a first container containing a first composition (A)
a second container containing a second composition (B), wherein the composition (A) comprises
(A1) less than 10% by weight of water and
(A2) one or more organic C1-C6 alkoxy silanes and/or their condensation products, and
the composition (B) comprises
(B1) water and
(B2) one or more terpenes, wherein the one or more terpenes are present in the second composition in an amount of from about 5 to about 8 weight percent, based on a total weight of the second composition.

19. The kit-of-parts according to claim 18, comprising separately packaged
a third container containing a third composition (C), wherein the third composition (C) comprises at least one coloring compound selected from the group of pigments and direct dyes.

20. The kit-of-parts according to claim 18, comprising separately packaged
a fourth container containing a fourth composition (D), the fourth composition (D) comprising at least one film-forming polymer.

* * * * *

UNITED STATES PATENT AND TRADEMARK OFFICE
CERTIFICATE OF CORRECTION

PATENT NO. : 12,233,147 B2
APPLICATION NO. : 17/601401
DATED : February 25, 2025
INVENTOR(S) : Torsten Lechner et al.

Page 1 of 1

It is certified that error appears in the above-identified patent and that said Letters Patent is hereby corrected as shown below:

In the Specification

Column 2, Line 60 change "$C_{1-6}$" to --$C_1$-$C_6$--.
Column 5, Line 55 change "R', R" and R'''" to --R',R" and R'''--.
Column 10, Line 13 change "$C_1$-C6" to --$C_1$-$C_6$--.
Column 11, Line 24 change "(A'''')-Si($R_{6"}$) $_{d"}$ (O$R_{5"}$) $_{e"}$" to --"(A'''')-Si($R_{6"}$)$_{d"}$ (O$R_{5"}$)$_{c"}$--.
Column 15, Line 5 change "$R_{11}$" to --$R_n$--.
Column 22, Line 58 change "sdisclosure" to --disclosure--.
Column 38, Line 46 change "omithine" to --orinithine--.
Column 38, Line 50 change "omithine to --orinithine--.
Column 38, Line 65 and 66 change "omithine" to --orinithine--.
Column 54, Line 29 change "%2 magnesium or %2 calcium" to --½ magnesium or ½ calcium--.
Column 57, Line 49 change "A,A',A",A'''and A''''" to --A,A',A",A''' and A"--.
Column 58, Line 24 change "$R_1$ $R_2$ N-L-Si (O$R_3$) $_a$($R_4$)$_b$" to --$R_9$ Si(O$R_{10}$)$_K$($R_{11}$)$_m$--.
Column 58, Line 59 change "αlpha-terpinene" to --alpha-terpinene--.

Signed and Sealed this
Fifteenth Day of July, 2025

Coke Morgan Stewart
*Acting Director of the United States Patent and Trademark Office*